United States Patent
Yakhini et al.

(10) Patent No.: US 9,898,578 B2
(45) Date of Patent: Feb. 20, 2018

(54) VISUALIZING EXPRESSION DATA ON CHROMOSOMAL GRAPHIC SCHEMES

(75) Inventors: Zohar Yakhini, Zikhron Ya'acov (IL); Robert Kincaid, Half Moon Bay, CA (US); Amir Ben-Dor, Bellevue, WA (US); Leslie A. Leonard, Portola Valley, CA (US); Nicholas M. Sampas, San Jose, CA (US)

(73) Assignee: Agilent Technologies, Inc., Santa Clara, CA (US)

(*) Notice: Subject to any disclaimer, the term of this patent is extended or adjusted under 35 U.S.C. 154(b) by 4133 days.

(21) Appl. No.: 10/817,244

(22) Filed: Apr. 3, 2004

(65) Prior Publication Data
US 2004/0241730 A1    Dec. 2, 2004

Related U.S. Application Data

(60) Provisional application No. 60/460,479, filed on Apr. 4, 2003.

(51) Int. Cl.
| G01N 33/48 | (2006.01) |
|---|---|
| G01N 33/50 | (2006.01) |
| G06F 19/26 | (2011.01) |
| G06F 19/12 | (2011.01) |
| G06F 19/24 | (2011.01) |
| G06F 19/18 | (2011.01) |
| G06F 19/20 | (2011.01) |

(52) U.S. Cl.
CPC ............. *G06F 19/26* (2013.01); *G06F 19/12* (2013.01); *G06F 19/18* (2013.01); *G06F 19/24* (2013.01); *G06F 19/20* (2013.01)

(58) Field of Classification Search
None
See application file for complete search history.

(56) References Cited

U.S. PATENT DOCUMENTS

| 4,383,994 | A | * | 5/1983 | McCully | 514/184 |
|---|---|---|---|---|---|
| 4,656,594 | A | * | 4/1987 | Ledley | 702/19 |
| 5,866,331 | A | * | 2/1999 | Singer et al. | 435/6 |
| 6,188,783 | B1 | | 2/2001 | Balaban et al. | |
| 6,391,551 | B1 | * | 5/2002 | Shultz et al. | 435/6.11 |
| 6,424,973 | B1 | | 7/2002 | Baclawski | |
| 6,519,583 | B1 | * | 2/2003 | Koleszar et al. | 707/1 |

(Continued)

OTHER PUBLICATIONS

Ben-Dor et al. RHO-Radiation Hybrid Ordering. Genome Research, vol. 10, 2000, pp. 365-378.*

(Continued)

*Primary Examiner* — Russell S Negin

(57) ABSTRACT

Systems and methods for displaying gene- and/or protein-related data with respect to chromosome maps at locations identifying relevant positioning of the genes with which the gene- and/or protein related data are associated. Multiple experiments may be plotted onto the display adjacent one or more chromosome maps. Automatic extraction of genomic location, based on accession numbers or other unique identifiers and cross connection with expression data is provided. Statistical assessments of correlations between expression and genome localization may be performed. Zooming capabilities, thumbnail/fullview toggling, browsability and linked data may be included as features of the visualization systems described.

77 Claims, 15 Drawing Sheets

(56) References Cited

U.S. PATENT DOCUMENTS

| | | | |
|---|---|---|---|
| 6,682,172 B2* | 1/2004 | Vanhooydonck et al. | 347/43 |
| 7,243,112 B2 | 7/2007 | Qu | |
| 7,472,137 B2 | 12/2008 | Edelstein et al. | |
| 2002/0004489 A1 | 1/2002 | Shi et al. | |
| 2002/0081597 A1* | 6/2002 | Lowe et al. | 435/6 |
| 2002/0174096 A1 | 11/2002 | O'Reilly | |
| 2003/0009295 A1 | 1/2003 | Markowitz et al. | |
| 2003/0139886 A1* | 7/2003 | Bodzin et al. | 702/28 |
| 2003/0224419 A1* | 12/2003 | Corcoran et al. | 435/6 |
| 2005/0034107 A1 | 2/2005 | Kendall et al. | |

OTHER PUBLICATIONS

Stanyon et al. Reciprocal chromosome painting shows that genomic rearrangement between rat and mouse proceeds ten times faster than between humans and cats. Cytogenetics and Cell Genetics. vol. 84, 1999, pp. 150-155.*

Anton. Elementary Linear Algebra, Fifth edition. John Wiley & Sons: New York, 1987, pp. 122-127.*

Pollack et al. Genome wide analysis of DNA copy-number changes using cDNA microarrays. Nature Genetics. vol. 23, 1999, pp. 41-46.*

Partridge et al. Location of candidate tumour suppressor gene loci at chromosomes 3p, 8p, and 9p for oral squamous cell carcinomas. International Journal of Cancer, vol. 83, 1999, pp. 318-325.*

Reeves A. MicroMeasure: A new computer program for the collection and analysis of cytogenetic data. Genome, vol. 44, 2001, pp. 439-443.*

Cuticchia et al. CMAP: contig mapping and analysis package, a relational database for chromosome construction. CABIOS, vol. 8, 1992, pp. 467-474.*

Schena et al. Parallel human genome analysis: Microarray-based expression monitoring of 1000 genes. PNAS, 1996, vol. 93, pp. 10614-10619.*

Definition of "chromosome map." Collins English Dictionary, 2000. Retrieved online Jul. 7, 2010 <<http://www.credoreference.com/entry/hcengdict/chromosome_map>>.*

Haefliger et al. Four novel members of the connexin family of gap junction proteins. The Journal of Biological Chemistry, vol. 267, 1992, pp. 2057-2064.*

Willecke et al. Six genes of the human connexin gene family coding for gap junctional proteins are assigned to four different human chromosomes. European Journal of Cell Biology, vol. 53, 1990, pp. 275-280.*

Golub et al. Molecular classification of cancer: Class discovery and class prediction by gene expression monitoring. Science, 1999, vol. 286, pp. 531-537.*

Metaphase Chromosome Spread. Dictionary of Developmental Biology and Embryology, Wiley, 2002, one page. Retrieved online on Oct. 18, 2011 from <<http://www.credoreference.com/entry/wileydevbio/metaphase_chromosome_spread>>.*

Pollack et al., "Microarray analysis reveals a major direct role of DNA copy number alteration in the transcriptional program of human breast tumors" PNAS, Oct. 1, 2002, vol. 99, No. 20, 12963-12968.

Hedenfalk et al.,"Molecular classification of familial non-BRCA1/BRCA2 breast cancer", PNAS, Mar. 4, 2003, vol. 100, No. 5, 2532-2537.

Ben-Dor et al., "Class Discovery in Gene Expression Data", Fifth Annual International Conference on Computational Molecular Biology, 2001, pp. 31-38.

Ben-Dor et al. "Tissue Classification with Gene Expression Profiles", J. Computational Biology, 2000, pp. 1-32.

Fujii et al., "A Preliminary Transcriptome Map of Non-Small Cell Lung Cancer", Cancer Research 62, 3340-3346, Jun. 15, 2002.

NCBI LocusLink, http://www.ncbi.nlm.nih.gov/LocusLink/, downloaded Apr. 3, 2003.

NCBI Entrez Genome, http://www.ncbi.nih.gov/mapview/map_search.cgi?taxid= 9606, pp. 1-2, downloaded Apr. 3, 2004.

NCBI Entrez Genome, "*Homo sapiens* genome data and search tips", http://www.ncbi.nlm.nih.gov/cgi-bin/Entrez/static/humansearch.html, pp. 1-30, downloaded Nov. 22, 2002.

Silicon Genetics, "Analysis, Clustering and Predictive Tools", http://www.silicongenetics.com/cgi/SiG.cgi/Products/GeneSpring/tools.smf, p. 1, downloaded Jul. 15, 2002.

Silicon Genetics, "Filtering Tools", http://www.silicongenetics.com/cgi/SiG.cgi/Products/GeneSpring/filter.smf?, p. 1, downloaded Jul. 15, 2002.

Silicon Genetics, "Predictive Tools (Machine Learning Algorithms)", http://www.silicongenetics.com/cgi/SiG.cgi/Products/GeneSpring/predict.smf?, p. 1, downloaded Jul. 15, 2002.

Silicon Genetics. "Hierarchical Clustering: Tree Building", http://www.silicongenetics.com/cgi/SiG.cgi/Products/GeneSpring/trees.smf?, p. 1, downloaded Jul. 15, 2002.

Silicon Genetics, "k-means Clustering", http://www.silicongenetics.com/cgi/SiG.cgi/Products/GeneSpring/Kmeans.smf?, p. 1, downloaded Jul. 15, 2002.

Silicon Genetics, "Self-organizing Maps", http://www.silicongenetics.com/cgi/SiG.cgi/Products/GeneSpring/SOM.smf?, p. 1, downloaded Jul. 15, 2002.

Silicon Genetics, "Principal Components Analysis", http://www.silicongenetics.com/cgi/SiG.cgi/Products/GeneSpring/PCA.smf?, pp. 1-2, downloaded Jul. 15, 2002.

Silicon Genetics, "Regulatory Sequence Search", http://www.silicongenetics.com/cgi/SiG.cgi/Products/GeneSpring/RegSeq.smf?, p. 1, downloaded Jul. 15, 2002.

Silicon Genetics, "Similarity Metrics", http://www.silicongenetics.com/cgi/SiG.cgi/Products/GeneSpring/sim_metrics.smf?, p. 1, downloaded Jul. 15, 2002.

"GeneSpring", www.silicongenetics.com, pp. 1-2, downloaded Nov. 22, 2002.

Silicon Genetics, "Tech Notes", http:www.silicongenetics.com/cgi/MasterPFP.cgi?doc= http://www.silicongenetics.com/c . . . , 5 pages, downloaded Nov. 22, 2002.

Caron H. et al., "The Human Transcriptome Map: Clustering of Highly Expressed Genes in Chromosomal Domains". vol. 291, pp. 1289-1292, Feb. 16, 2001.

Kent W. J. et al., "The Human Gerome Browser at UCSC". vol. 12, pp. 996-1006, May 16, 2002.

Kerlavage A. et al., "The Celera Discovery System", vol. 30, No. 1, pp. 129-136, Jan. 1, 2002.

Helt G. A. et al., "Bio Views: Java-based tools for geromic data visualization". vol. 8, No. 3, pp. 291-305, Mar. 3, 1998.

Siepel A. et al., "ISYS: a decentralized, component-based approach to the integration of heterogeneous bioinformatics resources". vol. 17, No. 1, pp. 83-94, 2001.

Ben-Dor a et al., "Class Discovery in Gene Expression Data". vol. conf. 3, pp. 31-38, Apr. 22, 2001.

Karp, Peter. An Ontology for Biological Function Based On Molecular Interactions. Oxford University Press. 2000. vol. 16. No. 3, pp. 269-285.

"Dealing With Measurement Noise", Chemical Engineering And Advanced Material. University of Newcastle Upon Tyne., 1996, 1-2.

European Patent Office, "EP Search Report", application EP05256067, Oct. 25, 2007.

Pinkel, et al., "High Resolution Analysis Of DNA Copy Number Variation Using Comparative Genomic Hybridization To Microarrays", Nature Genetics, New York, NY, Oct. 1998, 207-211.

Raychaudhuri, et al., "Associating Genes With Gene Ontology Codes Using A Maximum Entropy Analysis Of Biomedical Literature", Cold Spring Harbor Laboratory Press. Genome Research. vol. 12, Jan. 2002, 203-214.

Snijders, et al., "Assembly Of Microarrays For Genome-Wide Measurement Of DNA Copy Number", Nature Genetics, Nature America, New York, NY, Nov. 2001, 263-264.

Solinas-Toldo, et al., "Matrix-Based Comparative Genomic Hybridization: "Biochips to Screen for Genomic Imbalances"", Genes, Chromosomes & Cancer. vol. 20. No. 4, 1997, 399-407.

\* cited by examiner

VISUALIZING EXPRESSION DATA ON CHROMOSOMAL GRAPHIC SCHEMES

CROSS-REFERENCE

This application claims the benefit of U.S. Provisional Application No. 60/460,479, filed Apr. 4, 2003, which application is incorporated herein, in its entirety, by reference thereto.

FIELD OF THE INVENTION

The present invention pertains to software systems and methods for overlaying and visualizing data on chromosomal and genomic maps.

BACKGROUND OF THE INVENTION

The advent of new experimental technologies that support molecular biology research have resulted in an explosion of data and a rapidly increasing diversity of biological measurement data types. Examples of such biological measurement types include gene expression from DNA microarray or Taqman experiments, protein identification from mass spectrometry or gel electrophoresis, cell localization information from flow cytometry, phenotype information from clinical data or knockout experiments, genotype information from association studies and DNA microarray experiments, etc. This data is rapidly changing. New technologies frequently generate new types of data.

High-throughput techniques are generating huge amounts of biological data which are readily available, but which must still be interpreted. Experiments that measure thousands of genes and proteins (microarray, imminent protein-array technologies, etc.) simultaneously and under different conditions are becoming the norm in both academia and pharmaceutical/biotech companies. The ability to visualize this data in a meaningful way is an important consideration in making this data more accessible and widely used.

Tools that allow a user to visualize meaningful data by sorting and/or presenting the data in a way which is more ordered or more easily interpretable by the human viewer are needed for making the data readily accessible and widely useable by researchers. Such tools and visualization methods could also prove useful to clinician-researchers in accessing such data to classify different tissue types, e.g., tumor types, with the goal of deciding upon a therapeutic regimen. Such visualization tools may ultimately be used as aids by physicians to explain test results to patients.

The Entrez Map Viewer provided by the National Center for Biotechnology Information (NCBI) provides graphical displays of features on NCBI's assembly of human genomic sequence data as well as cytogenetic, genetic, physical, and radiation hybrid maps. The Entrez Map Viewer integrates human sequence and map data from a variety of sources, and displays various types of maps including sequence, cytogenetic, genetic linkage, radiation hybrid and YAC contig.

Among the mapping or visual display features available to the Entrez Map Viewer, the sequence maps provide localization of FISH mapped clones. When a clone insert sequence is used for contig assembly and if it spans a large region (e.g., >1 Mb), the clone is also marked to span the same region. Component maps show components of the human genome assembly by showing the placement of individual GenBank sequence entries that were used to generate the genomic contigs. This represents a tiling path for the human genome sequence, based on the relationship of overlapping clones. Contig maps show the chromosomal placement of contigs that have been assembled at NCBI using finished and draft high-throughput genomic (HTG) sequence data. Any individual contig can be assembled from finished sequence (phase 3 HTG), draft sequence (phase 1 and 2 HTG), or a mixture of both. CpG Island maps show regions of high G+C content on the assembled genome sequence.

The dbSNP haplotype map displays intervals of contig sequence when there is information in dbSNP to define chromosomal haplotypes. Typically, there is more than one haplotype allele at any sequence location, and the set of alleles revealed in a particular experiment as a dbSNP Haplotype Set is referenced. The verbose text for the dbSNP_Hap map gives the submitter handle and local haplotype set IDs for the interval. Haplotype set features are linked to the dbSNP Hapset display page where all haplotypes in the set are displayed. Haplotype sets from different labs may be presented side by side when they span a common interval of contig sequence.

The GenBank DNA map shows the placement of human genomic DNA sequences from GenBank that were not used in the assembly of contigs. The placement is based on the alignment of the sequences to the components of the contigs. The GenBank DNA map includes human genomic sequences longer than 500 bp that have at least 97% identity to the components for at least 98 base pairs. If a sequence extends beyond a contig, that portion of sequence is not shown. A "hits" link is provided which, when selected, leads to a tabular display that shows the matching regions (base spans) of the assembly component and the GenBank genomic DNA record that has been aligned to it.

Gene_Sequence maps identify genes that have been annotated on the genomic contigs. These include known and putative genes placed as a result of alignments of mRNAs to the contigs. If multiple models exist for a single gene, corresponding to splicing variants, the Gene_Sequence map presents a flattened view of all the exons that can be spliced together in various ways. A GenomeScan map uses models generated by Genome Scan in which mRNA alignments were used to segment the genomic sequence by putative gene boundaries, and GenomeScan was executed on these segments to predict genes. Sage Tag Map provide maps of SAGE tag sequences aligned to the genomic contigs, and provide connections to SAGEmap, NCBI's resource for serial analysis of gene expression data.

STS maps provide placement of STSs from a variety of sources onto the genomic data using electronic-PCR (e-PCR). The markers are from RHdb. GDB, GeneMap'99, (gene-based markers) Stanford G3 RH map (both gene and non-gene markers), TNG map, Whitehead RH map and YAC maps (both gene and non-gene markers), Genethon genetic map, Marshfield genetic map, and several chromosome-specific maps, such as the NHGRI map for chromosome 7 and the Washington University map of chromosome X. Transcript (RNA) maps are diagrams of the RNAs that are predicted on the genomic contigs. The Transcript map shows the combinations of exons (i.e., splice variants) that are valid, based on mRNA sequences.

The UniGene_Human map displays human mRNA and EST sequences aligned to the assembled human genomic sequence that has been repeat-masked and dusted. Only ESTs supplied with orientation are used. Each alignment is the single best placement for that sequence in the current build of the human genome. The display of the UniGene_Human map varies according to the span of sequence being displayed. For large spans of sequence (greater than 10 million bases), the Map Viewer displays histograms that show the density of ESTs and mRNAs aligned to a region, the UniGene clusters to which they belong, and the number of sequences from each UniGene cluster. For smaller spans of sequence (i.e., higher resolutions, showing less than 10 million bases), the Map Viewer displays the above information, plus blue lines that indicate exon/intron structure.

A current implementation for visualizing genomic gene expression data from microarrays is provided by GeneSpring 5.0, available from Silicon Genetics, of San Carlos, Calif.). GeneSpring 5.0 provides a genome browser for displaying genes of interest or all of the genes in a genome view. The genes may be displayed as vertical bars along horizontal lines, corresponding to their positions along the chromosomes where they are located. The browser provides zooming capabilities wherein a portion of the genome map may be expanded to view in greater detail, but this view does not maintain focus and context. Thus, only one mapping view at a time is available and the user must continuously switch between screens if any comparisons among different views are to be made.

A genome-wide transcriptome map of non-small cell lung carcinomas based on gene-expression profiles generated by serial analysis of gene expression (SAGE) was constructed as reported in Fujii et al., "A Preliminary Transcriptome Map of Non-Small Cell Lung Cancer", Cancer Research 62, 3340-3346, Jun. 15, 2002. An overlay of four experiments (4 representative sets) was displayed on a transcriptome map, with the expression information being extracted and mapped via SAGE.

While some limited mapping of information to transcriptome maps has been experimented with, it would be further desirable to provide tools and techniques for not only presenting gene expression data and other types of data on genomic maps representing the loci where the genes responsible for the expression data exist, or for mapping biomolecule abundance to corresponding gene/chromosome locations (including mapping of CGH gene amplification/deletions; mRNA expression, protein abundance, and the like), but for more transparently and automatically correlating such data with appropriate placement on the maps. Further, correlation with other map formats and automatic linking between such formats would be desirable. Still further, the ability to visualize more than just the bare expression data would be desirable, whether appearing on the face of the visualization or otherwise embedded, but accessible at the will of the user. Further desirable would be the provision of such maps having interactive capability so that the user can alter the data that is displayed.

SUMMARY OF THE INVENTION

The present invention provides methods and systems for overlaying gene-related data with respect to chromosome maps. Arbitrary gene-related data may be imported and manipulated to display such data in positions relative to chromosome maps which are indicative of positions of the genes which the data relate to. Multiple experiments may be plotted onto the display adjacent one or more chromosome maps. The arbitrary gene-related data have identifiers for determining genetic loci of the genes on the chromosome maps. The present invention may automatically read such identifiers and match the identifiers with predefined identifiers on at least one of the chromosome maps. Once matching has been performed the gene-related data is reordered according to the order of gene location, and displayed along side the one or more chromosome maps.

The identifiers associated with the arbitrary gene-related data may be GenBank accession numbers, RefSeq accession numbers, UniGene Cluster ID's, UniGene ID's, official standard gene names, LocusLink ID's or other well known identification systems.

The matching may be performed by providing a relational database which stores a set of cross-referenced tables for matching the identifiers with said predefined identifiers, and as the identifiers are read, they are matched with the predefined identifiers in the cross-referenced tables through standard database queries.

The arbitrary gene-related data may comprise gene expression data and may be inputted in tabular form. Examples of tabular format that may be used include, but are not limited to, tab-delimited text files, Excel spreadsheets, database queries, and the like. The actual data represented in these formats may include, but are not limited to gene expression data, CGH data, protein abundance data, any DNA, mRNA or protein measurement, etc. The only restriction is that whatever data is used must be capable of being mapped to a chromosome location in order to be plotted in context. Additional information, annotations, statistical data, and the like may be additionally or alternatively displayed relevant to the one or more chromosome maps.

Statistical assessments of co-location may be represented on the visualizations prepared according to the present invention. For example, when there are two classes of samples, such as a tumor class and a "normal" (i.e., no evidence of tumor) class, researchers are interested in finding chromosomal regions in which there is a statistically significant concentration of genes that separate the two classes very sharply. The present invention annotates these concentrations on the visualizations. Operons are examples where there is a functional meaning in the regulation of co-location of genes. Statistical methods according to the present invention may detect such types of related activity.

Row vectors of gene-related data may be calculated using an auxiliary process to obtain cluster data describing the gene-related data. The cluster data may be displayed in locations relative to the locations of the displayed gene-related data.

A matrix containing gene expression microarray data may be inputted, wherein each row of the matrix is associated with a particular gene, and wherein each column of the matrix is associated with a microarray experiment, wherein a portion of the total number of columns are associated with experiments taken from normal, healthy tissue, and another portion of the total number of columns are associated with experiments taken from tissue exhibiting a known abnormality. As noted, gene expression data is only an example of a data type that may be inputted, and the present invention is not restricted to use with gene expression data or microarray data as many other types of data may be used as inputs. The matrix may be divided into two smaller matrices with a first matrix containing the columns associated with normal experiments and a second matrix containing the columns associated with abnormal experiments. The first and second matrices are reordered and displayed relative to one or more chromosome maps. Relevance scores of the rows of the matrices may be calculated to identify genes that are likely to be good "separators" which indicate the existence of the abnormality being considered. The relevance scores may be mapped relative to chromosomal locations.

Relevance density scores may be calculated as a tool to search for relatively dense areas or groupings of good "separator" genes on any particular chromosome map.

Chromosomal copy number abnormality data may be matched by identifiers and mapped to the chromosome maps, similarly to expression data. Likewise, relevance assessment and relevance density scores of chromosomal copy number abnormality data may be calculated, mapped and/or assessed.

Additional gene-related information such as polymorphism measurements, annotations, transcription factor binding sites, RNA expression values, allele information, alternative exon splicing data, mRNA expression levels, protein abundance, gene amplification/deletion data, other biomolecule abundance data, and other "biomolecule abundance" mapping (including, but not limited to CGH gene amplification/deletions), and/or presence of motifs in the regulatory regions of genes may also be matched and mapped relative to gene/chromosome locations.

The present invention provides advantageous features including visualizations of an entire data set (such as a genome), with or without additional displays of zoomed and detailed views on the same display, thereby foregoing the need to toggle between views, allowing the viewer to simultaneously maintain focus and context of an area of interest.

The present systems may provide automatic extraction of genomic locations of gene-related data, statistical assessment of co-location and visualization of the same, and/or viewing of additional information as color-coded columns, histograms and/or textual information to provide richer detail of the material being studied. The present systems may provide zooming capabilities, thumbnail and/or full view toggling, browsability and data linking capabilities with regard to the visualized display.

The statistical means provided to assess correlations between expression and genome localization may provide useful tools for diagnosing and/or identifying disease-related genes.

The system may provide interactivity, whereby a user may change data inputs, data displays, etc. at will and perform statistical analyses as desired.

These and other advantages and features of the invention will become apparent to those persons skilled in the art upon reading the details of the systems, methodologies and tools as more fully described below.

DETAILED DESCRIPTION OF THE INVENTION

Figure 1:
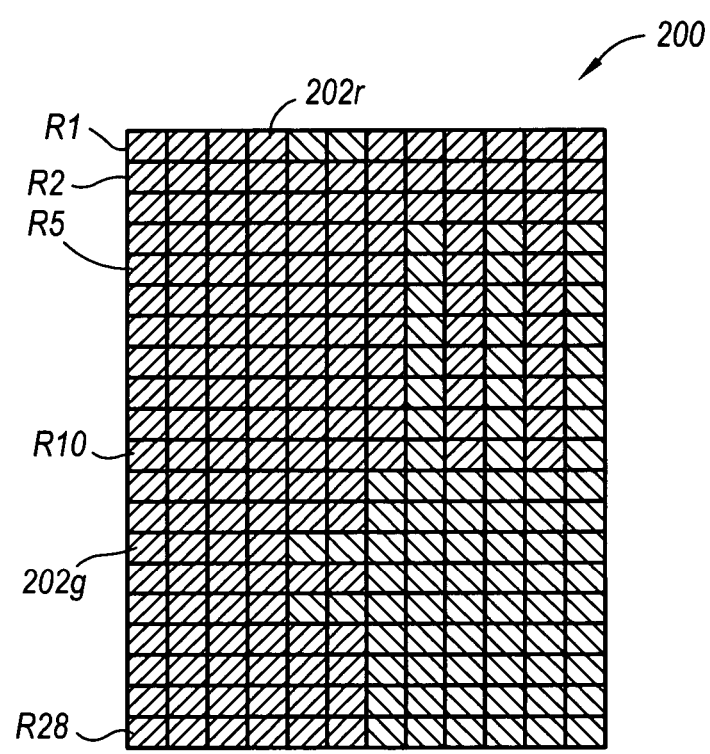
FIG. 1 shows an example of a portion of a conventional heap map visualization in which expression data is visualized in matrix format.

Before the present tools and techniques are described, it is to be understood that this invention is not limited to particular data sets, analysis techniques or steps described, as such may, of course, vary. It is also to be understood that the terminology used herein is for the purpose of describing particular embodiments only, and is not intended to be limiting, since the scope of the present invention will be limited only by the appended claims.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are now described. All publications mentioned herein are incorporated herein by reference to disclose and describe the methods and/or materials in connection with which the publications are cited.

It must be noted that as used herein and in the appended claims, the singular forms "a", "and", and "the" include plural referents unless the context clearly dictates otherwise. Thus, for example, reference to "a gene" includes a plurality of such genes and reference to "the data set" includes reference to one or more data sets and equivalents thereof known to those skilled in the art, and so forth.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

Definitions

The term "color coding" refers to a software technique which maps a numerical or categorical value to a color value, for example representing high levels of gene expression as a reddish color and low levels of gene expression as greenish colors, with varying shade/intensities of these colors representing varying degrees of expression. Color-coding is not limited in application to expression levels, but can be used to differentiate any data that can be quantified, so as to distinguish relatively high quantity values from relatively low quantity values. Additionally, a third color can be employed for relatively neutral or median values, and shading can be employed to provide a more continuous spectrum of the color indicators.

The term "down-regulation" is used in the context of gene expression, and refers to a decrease in the amount of messenger RNA (mRNA) formed by expression of a gene, with respect to a control.

The term "gene" refers to a unit of hereditary information, which is a portion of DNA containing information required to determine a protein's amino acid sequence.

"Gene expression" refers to the level to which a gene is transcribed to form messenger RNA molecules, prior to protein synthesis.

"Gene expression ratio" is a relative measurement of gene expression, wherein the expression level of a test sample is compared to the expression level of a reference sample.

A "gene product" is a biological entity that can be formed from a gene, e.g. a messenger RNA or a protein.

A "heat map" or "heat map visualization" is a visual representation of a tabular data structure of gene expression values, wherein color-codings are used for displaying numerical values. The numerical value for each cell in the data table is encoded into a color for the cell. Color encodings run on a continuum from one color through another, e.g. green to red or yellow to blue for gene expression values. The resultant color matrix of all rows and columns in the data set forms the color map, often referred to as a "heat map" by way of analogy to modeling of thermodynamic data.

An "item" refers to a data structure that represents a biological entity or other entity. An item is the basic "atomic" unit of information in the software system.

A "microarray" or "DNA microarray" is a high-throughput hybridization technology that allows biologists to probe the activities of thousands of genes under diverse experimental conditions. Microarrays function by selective binding (hybridization) of probe DNA sequences on a microarray chip to fluorescently-tagged messenger RNA fragments from a biological sample. The amount of fluorescence detected at a probe position can be an indicator of the relative expression of the gene bound by that probe. Any given microarray may employ a single channel or single color platform on which only a single experiment is run, or a multi channel or multi color platform on which multiple experiments are run. A common multi channel example is a two channel platform where one experiment is color-coded with a first color (e.g., color-coded green) and the other channel is color-coded with a second color (e.g., color-coded red). Such an arrangement may be used to simultaneously run a reference sample (experiment) and a test sample (experiment) and differential expression values may be calculated from a comparison of the results.

"CGH data" refers to data obtained from "Comparative Genomic Hybridization" measurements. CGH involves a technique that measures DNA gains or losses. Some techniques perform this at the chromosomal level, while newer emerging techniques, such as "Array CGH" (aCGH) use high throughput microarray measurements to measure the levels of specific DNA sequences in the genome. While not specifically limited to aCGH data, the present invention is applicable to aCGH data, which comes in a form analogous to array-based gene expression measurements.

The term "promote" refers to an increase of the effects of a biological agent or a biological process.

A "protein" is a large polymer having one or more sequences of amino acid subunits joined by peptide bonds.

The term "protein abundance" refers to a measure of the amount of protein in a sample; often done as a relative abundance measure vs. a reference sample.

"Protein/DNA interaction" refers to a biological process wherein a protein regulates the expression of a gene, commonly by binding to promoter or inhibitor regions.

"Protein/Protein interaction" refers to a biological process whereby two or more proteins bind together and form complexes.

A "sequence" refers to an ordered set of amino acids forming a protein or to an ordered set of nucleic acid bases forming a DNA fragment or an RNA molecule.

The term "overlay" or "data overlay" refers to a user interface technique for superimposing data from one view upon data in a different view; for example, overlaying gene expression ratios on top of a chromosome view.

A "spreadsheet" is an outsize ledger sheet simulated electronically by a computer software application; used frequently to represent tabular data structures.

The term "up-regulation", when used to describe gene expression, refers to an increase in the amount of messenger RNA (mRNA) formed by expression of a gene, with respect to a control.

The term "UniGene" refers to an experimental database system which automatically partitions DNA sequences into a non-redundant sets of gene-oriented clusters. Each UniGene cluster contains sequences that represent a unique gene, as well as related information such as the tissue types in which the gene has been expressed and chromosome location.

The term "view" refers to a graphical presentation of a single visual perspective on a data set.

The term "visualization" or "information visualization" refers to an approach to exploratory data analysis that employs a variety of techniques which utilize human perception; techniques which may include graphical presentation of large amounts of data and facilities for interactively manipulating and exploring the data.

Expression data is typically visualized in matrix format, when dealing with a plurality of measured samples. This is the case for almost all publications in the area and for the software packages that dominate the existing expression data analysis market. FIG. 1 shows an example of a portion of a conventional heat map visualization 200, in which expression data is visualized in matrix format. A standard heat map visualization such as visualization 200 is a static visual representation of a tabular data structure of gene expression values, wherein color-codings are used for displaying numerical values. The numerical value for each cell 202 in the data table is encoded into a color for the cell. Color encodings run on a continuum from one color through another, e.g. green 202g to red 202r or blue to yellow for gene expression values.

Standard heat map visualizations have significant shortcomings as to their usefulness for performing visual correlation analyses. Since these displays are static, the cells in the display 200 cannot be manipulated to form different combinations or views in attempting to find similarities among the experimental data. Further, as noted above, the sheer volumes of data that are generated by current experimental data generating procedures, such as microarray procedures and protein expression measurements, for example, makes it generally impossible to display the contents of all the data that needs to be reviewed on a single display in any form that is visually distinguishable by the user.

Furthermore, associating any of these values with the locations of the genes (from which the values were generated) on a chromosome map has heretofore been an extremely tedious, manual process of selecting a value or values of interest to be associated with the chromosome map. Even if a chromosome map having experimental data overlaying locations of the genes from which the data has been derived is constructed, such a map would still require the user to additionally switch between screen views to search for statistical data and means by which to assess correlations between expression data and genome localization.

Each row (R1, R2 . . . R28) of the matrix 200 represents the expression levels of a gene across a set of measured samples (experiments), with the results of each microarray experiment being expressed in respective columns. As noted above, matrix 200 shows only a portion of the microarray experiments. It is not unusual for the full matrix to contain thousands of rows.

Figure 2A:
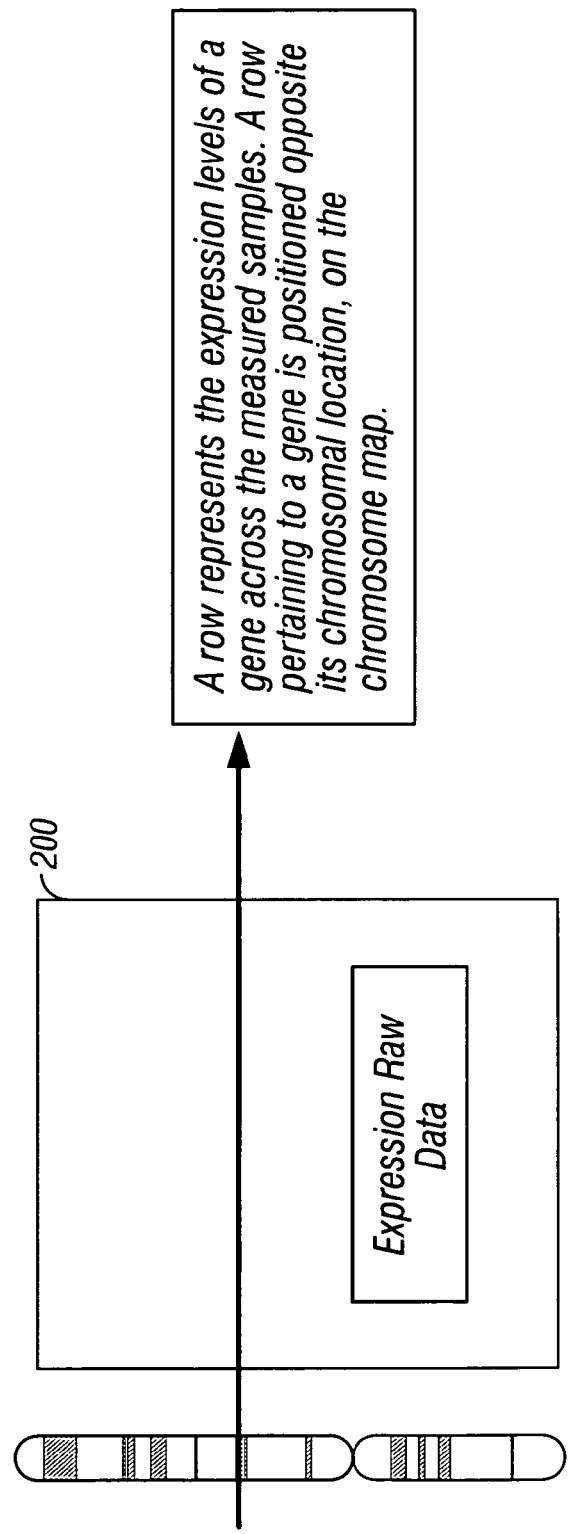
FIG. 2A is a schematic diagram illustrating a first tool useful for associating expression data with genome locations according to the present invention.
Figure 2B:
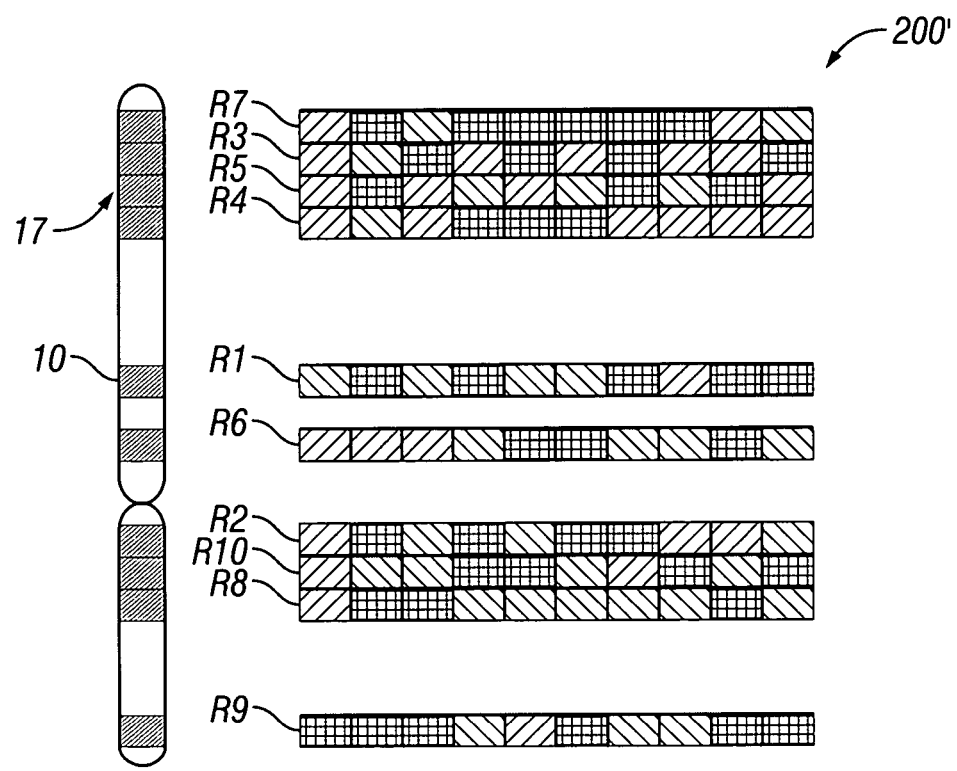
FIG. 2B is a schematic diagram illustrating a display of expression data with respect to one chromosome, after reordering and spatially arranging the rows of a heat map to correspond to genetic chromosomal locations.

Referring to FIG. 2A, a first tool useful for associating expression data with genome locations is described with reference thereto. When a heat map, such as heat map 200 is inputted to the present system, a determination is made, from the gene identifiers associated with the rows of the matrix 200, as to where the genes are located on their associated chromosomes. Reordering and spatial grouping of the rows of matrix 200 are automatically performed by the system, based on the gene identifiers, to correspond with the locations of the genes on the chromosomes. While it is possible that experiments specific to one particular chromosome that the user is interested in looking at might be performed over an entire microarray, it is generally more often the case that a given microarray design will include genetic data pertaining to more than one chromosome. In the case of a microarray having only data for one chromosome, the results of the reordering would appear as schematically shown in FIG. 2B. In this example, a 10×10 matrix 200' (containing rows R1-R10 for genes 1-10 and columns 1-10 pertaining to experiments 1-10) is shown after reordering and spatial grouping, wherein all of the genetic information contained within the 10×10 matrix pertains to chromosome 17. Note that the reordered matrix 200' shown in FIG. 2B is not only reordered as to the sequence in which the rows of information appear, but they are also spatially reordered, so as to spatially group the rows to more closely conform to the actual locations on the chromosome where the genes (represented by the expression data in the rows) appear on the chromosome.

For a case where the data in a microarray pertains to more than one chromosome, maps of each chromosome that pertain will be displayed, along with the rows of data that pertain to that chromosome being displayed along side that chromosome across from the relative locations where those genes are found on that particular chromosome. As a result, a plurality of side by side visualizations similar to that shown in FIG. 2B will be displayed, one for each chromosome for which data is represented in the original full microarray matrix, with a sub-matrix associated with each chromosome containing only those rows of data for genes which are associated with the respective chromosome, ordered and spaced according to the gene locations on the chromosome.

In order for the present invention to represent arbitrary gene-related data mapped to a chromosome location, it is necessary to correlate such data with the appropriate genetic locus. This is true whether the arbitrary gene-related data is in the form of a heat-map or some other form inputted to the system, such as raw data, numerical matrix data, etc. Advantageously, this mapping is not required to be made at the time experiments are designed, performed or analyzed. All that is required is that each datum to be mapped has a suitable identifier to specify its genetic locus. Common exemplary identifiers are GenBank or RefSeq accession numbers, UniGene Cluster ID's, official standard gene names, etc. The present invention provides an automated facility for constructing these mappings, in real-time or otherwise.

One example of a facility for providing a suitable identifier to specify a genetic locus of each datum is provided in co-pending, commonly assigned application Ser. No. 10/154,529 filed May 22, 2002 and titled "Biotechnology Information Naming System", which is incorporated herein, in its entirety, by reference thereto. Application Ser. No. 10/154,529 describes a computer system that serves to resolve bio-molecular identification numbers and names with alternate identification designations as well as annotation information. This facility can programmatically return such ID's and annotation in real-time, for a given RefSeq accession number, UniGene ID, or LocusLink ID, which includes the LocusLink curated chromosome location.

Another approach to providing a suitable identifier to specify a genetic locus of each datum involves the use of a traditional relational database which stores a set of suitable cross-referenced tables. In this approach, as data is imported into the present system for viewing, each ID corresponding to each datum as it enters the system is associated with a chromosome location through standard database queries.

The local database is regularly updated from external databases, incorporating increments and corrections to chromosome location, as well as to sequence identification and function.

Regardless of the specific technique used, the present invention provides a facility for automatically mapping datum ID's to chromosome locations. The present invention does not need to store chromosome location, but this information may be retrieved at the time of the display. The present system can draw the information from the current version of the database, so that the information is always up to date. Alternatively, the locations could be stored, so there can be an option of using static, stored chromosome locations, or locations which are dynamically generated as the genetic data is read into the system.

In either case, the rows of an inputted matrix are rearranged by row order and spatially arranged so that the genes represented by the rows of the expression matrix are arranged in one or more new matrices corresponding to (and representative of) the gene order of the chromosomal locations. Chromosomes and cytobands 10 are displayed along the left (or right) axis of each matrix. A row represents the expression levels of a gene across the measured samples. A row pertaining to a gene is positioned opposite its chromosomal location, on the chromosome map.

In this way, a single experiment, containing expression data for a series of genes, up to an entire set of arrays, represented by a matrix, can be mapped to the appropriate chromosomal locations. Rather than presenting single length histogram representations of expression levels along side the chromosome maps, entire rows, such as from a heat map, can be associated with the chromosome maps.

Figure 3A:
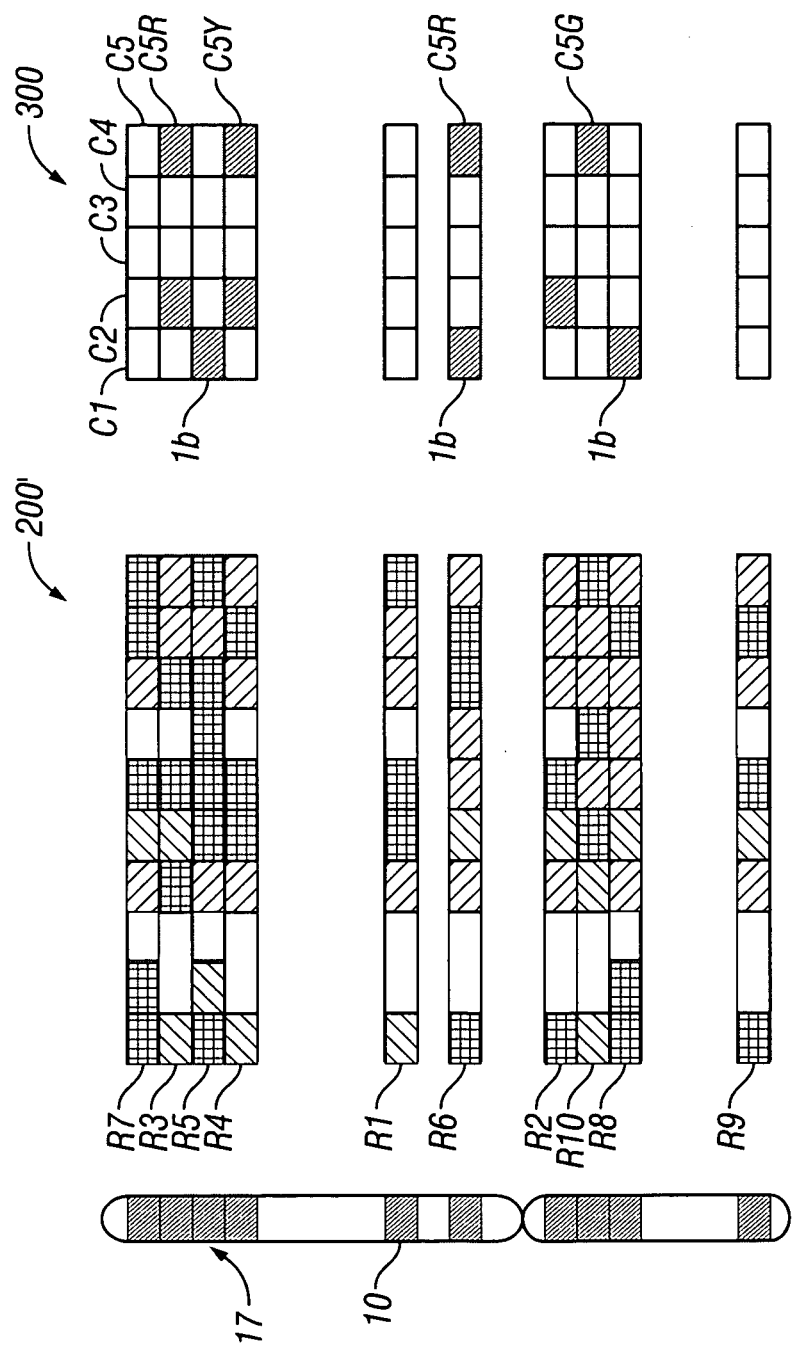
FIG. 3A schematically shows a visualization in which an additional matrix has been displayed along side the matrix shown in FIG. 2B.

Additional matrices may be displayed alongside the expression matrix associated with each chromosome map and may contain information indicative of many types of information/annotation. For example, FIG. 3A shows a visualization in which an additional matrix 300 has been displayed along side the matrix 200' referring back to the example shown in FIG. 2B. In this case, matrix 300 contains columns of annotation information characterizing the expression values for the genes expressed in expression matrix 200'. Column C1 indicates whether the gene is a kinase. Column C2 indicates "cancer-related". Columns 3 and 4 pertain to cellular localization of the genetic material (nucleus and mitochondria, respectively). That is, a chromosome equivalent may be mapped for mitochondrial DNA, or any other cellular DNA that is being investigated in a measurement assay.

Column 5 indicates cluster data, indicating which cluster or clusters the expression data may belong to. The present invention is not to be limited to the particular types of annotation information described herein, as many other types of annotations (e.g., color coded protein structural families, color-coded cellular location (ribosomal, membrane, etc.), color-coded homology to other organisms, oncogenes, tumor-supressor genes, etc.), any gene ontology (GO) annotation categories, etc. may be included similarly, as would be readily apparent to one of ordinary skill in the art after reading the present disclosure.

Cluster data is generated by taking row vectors of the expression material and clustering them according to how similar they are, as is known in the art. Each of the columns may include color indicators to characterize the expression data with which they are associated. With regard to cluster data, different identified clusters may be assigned different colors. In the example shown in FIG. 3A, a first identified cluster is coded red and indicated by reference numeral C5R in column C5, a second identified cluster is coded yellow and indicated by reference numeral C5Y in column C5, and a third identified cluster is coded green and indicated by reference numeral C5G in column C5. As can be seen by referring to the visualizations in FIG. 3A, rows R3 and R6 of the expression data in matrix 200' belong to cluster 1 as noted by the red indicators in column 5, row R4 belongs to cluster 2 and row R10 belongs to cluster 3.

Figure 3B:
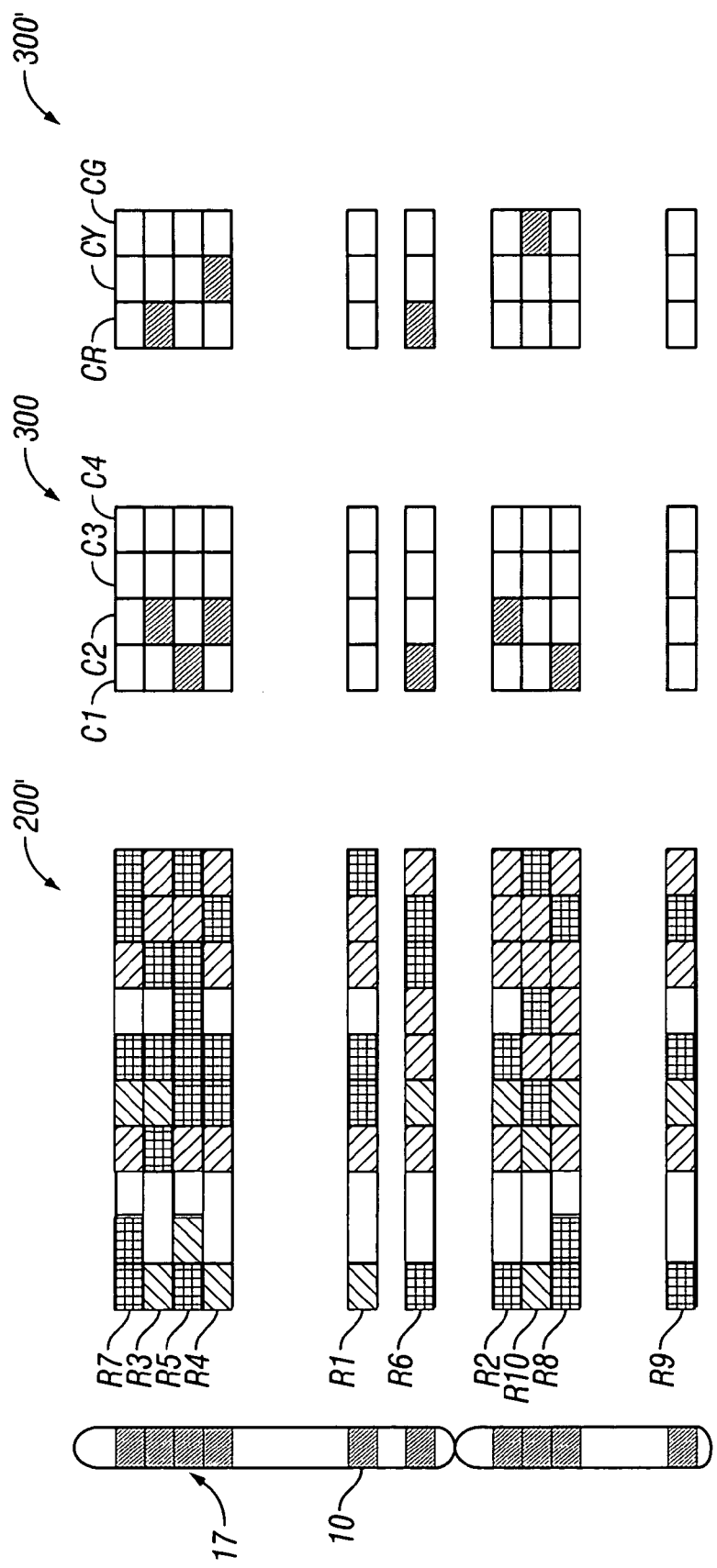
FIG. 3B schematically shows a variation of the visualization of FIG. 3A, particularly with regard to the display of the additional matrix.

Alternatively, the cluster annotations may be arranged in matrix format 300' as shown in FIG. 3B, so that all red indicators are aligned in one column CR, all yellow indicators in a second column CY, all green indicators in a third column CG, etc. This can be useful where a row of expression values might belong to more than one defined cluster.

Likewise, the annotations in the other columns of matrix 300 may be color-coded for easier identification. For example, in FIG. 3A, the indicators 1b in column 1 (Kinase) have been color-coded blue.

The rows of expression values in matrix 200 or 200' can be scored based on how well they separate tumor cells (cancer) from normal cells. For example, when a gene is very active in a cell that has cancer, but has relatively low activity or is inactive in a normal, non-cancerous cell (or vice versa) can be a good indicator/identifier of cancerous tissue. Such genes can have diagnostic potential, and perhaps tell a researcher what type of treatment is needed based upon reading expression levels indicative of a particular type of cancer.

Figure 4:
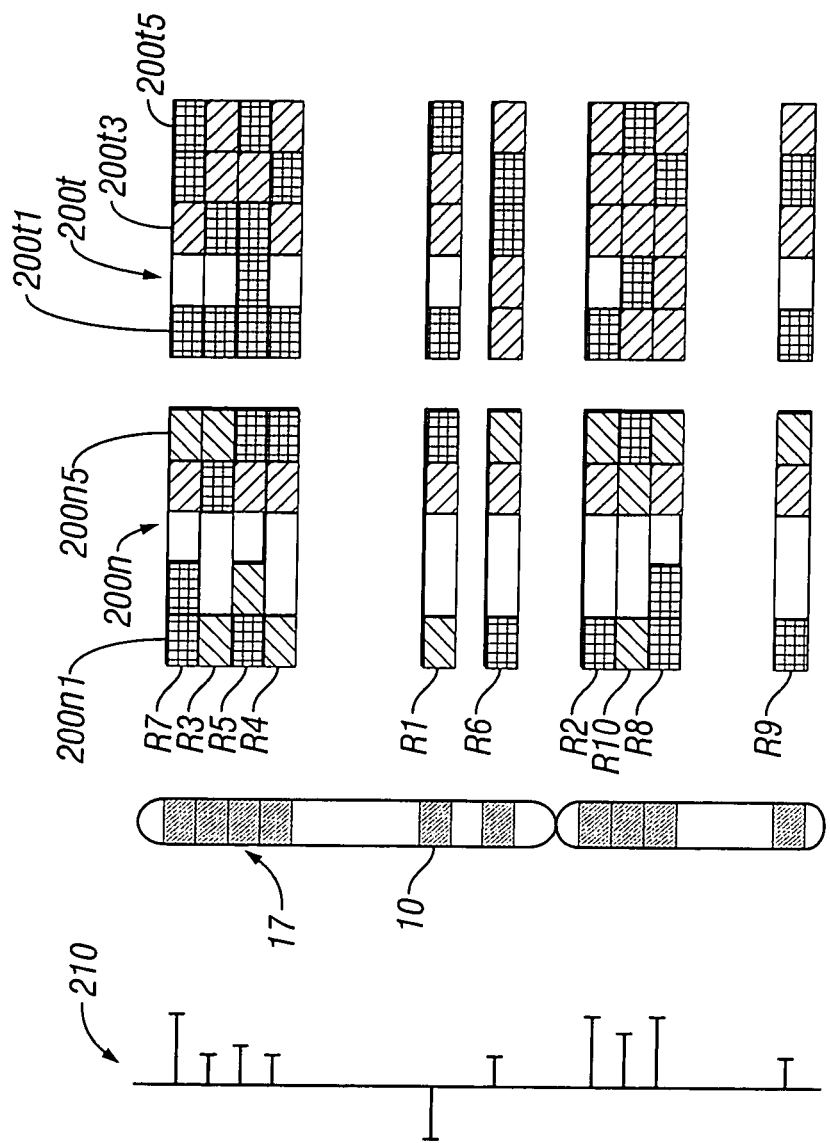
FIG. 4 is a schematic diagram of a visualization displaying expression data with respect to one chromosome, after reordering and spatially arranging the rows of a heat map to correspond to genetic chromosomal locations, in addition to dividing the heat map matrix into two matrices to represent normal and abnormal tissues. Additionally, relevance values are plotted relative to the positions of the genes represented by the expression data.

In known experiments in which both tumor and normal cells are experimented upon, a resultant array (matrix) 200 of expression values can be separated into two matrices, one 200n of which contains columns (experiments) containing expression values for normal tissues which were experimented upon, while the second 200t contains columns (experiments) containing expression values for the same genes, but which genes belonged to known cancerous (tumor) tissues, as shown diagrammatically in FIG. 4. Such tumor cells may be taken from one or more actual patient biopsies, from cell lines, or from some other tumor cell source. In the diagrammatic example of FIG. 4, we have shown that five experiments were run on normal tissues (hence, five columns resulting in matrix 200n) and five experiments were run on tumor tissues (five columns of data in matrix 200t).

Alternatively, a single matrix 200 can be ordered in the same way, so that normal experiments are all on one side and tumor experiments are all on the other side. For the example in FIG. 4, a single 10×10 matrix may be arranged in which the first five columns of data pertain to normal tissues and the second five columns of data pertain to the tumor tissues, or vice versa.

A row which contains a good separator gene will show predominantly green indicators in one of the normal or tumor matrices (or sides of a single matrix) and predominantly red indicators in the other of the normal or tumor matrices (or sides of a single matrix), for example. That is, if a gene is highly expressed in one set and not in the other, this is a gene that has diagnostic potential. Relevance scores or p-values either color coded or represented as lengths of varying lines can score genes according to how well they separate tumors from normals, based on their expression values.

The "−log p value" (relevance score) gives the separation value of the particular gene being analyzed. Log p value is very negative if probability is very close to zero (very rare event), such as when a gene is highly expressed in one set and not in the other. Therefore negative log p becomes a large value, indicating that this is a good separator. The relevance scores can be displayed in a line map 210 (as shown in FIG. 4, for example), or in a color map, like the way that gene expression levels are displayed in a heat map, or in binary coding, for example. The directionality of the scores indicates whether a first class of scores is larger than a second class of scores, or vice versa.

Scoring Genes for Relevance

Relevance information is useful in identifying genes driving the biological process, in selecting small subsets of genes with diagnostic potential, and in better understanding the condition studied and its relationship to known or hypothesized biochemical pathways. In addition to relevance scoring, classification techniques may be applied which employ varying relevance-based selected sets of genes to further characterize the data.

Some of the genes measured in an experiment may play a major role in the processes that underlie the differences between the classes (e.g., between tumor and normal tissue) or are greatly effected by the differences. Such genes are highly relevant to the studied phenomenon. On the other hand, the expression levels of many other genes in the experiment may be irrelevant to the distinction between tissue classes.

Attaching a measure of relevance to each gene in the experiment is useful in several ways. By seeking small sets of genes that can jointly serve as a classifier and as a basis for the development of diagnostic assays, one can choose amongst the more informative genes found in preliminary more comprehensive studies. Highly informative genes that are parts of known biochemical pathways give insight into the processes that underlie the differences between classes. Highly informative genes (or ESTs) of unknown function suggest new research directions.

The following describes an exemplary, non-limiting technique which may be used for relevance scoring of genes:

In this example, the experimental data set is defined as D, and consists of pairs $(x_i, l_i)$ for i=1, . . . , M. Each sample $x_i$ is a vector in $R^N$ that describes the expression values of N genes/clones. The label $l_i$ associated with $x_i$ is either positive or negative (i.e., + or −). For simplicity, this explanation is given with regard to two-label classifications, although it would be readily appreciated, by those of ordinary skill in the art after reading the present description, that these techniques may be applied to three- and many greater numbers of classifications. Four scores for the genes are examined in this example. The first, TNoM, is a combinatorially derived score that depends only on the vector of class labels that results from putting the expression levels $x_1(g), \ldots, x_m(g)$ in ascending order and permuting $l_1, \ldots, l_m$ accordingly. The second, "Info", is an information-theoretic score that also depends only on that order. The third score is based on logistic regression and depends on actual expression values. Finally, Gaussian-based scores are also described. Numerical values for relevance scores mean a lot more if they come with statistical significance figures. This description also addresses statistical significance figures.

The TNoM score (Threshold Number of Mis-classification) is based on searching for a simple rule that uses a given expression level, for the given gene, to predict the label of an unknown. Formally, a rule is defined by two parameters a, and b. The predicted class is simply sign(ax+b). Since only the sign of the linear expression matters, attention can be limited to a ∈{−1,+1}. A natural approach is to choose the values of a and b to minimize the number of errors:

$$Err(a, b | g) = \sum_i 1\{l_i \neq \text{sign}(a \cdot x_i[g] + b)\} \quad (1)$$

where $x_i[g]$ is the expression value of gene g in the $i^{th}$ sample. The best values are found by exhaustively trying all 2(m+1) possible rules. Attention is limited to threshold values that are mid-way points between actual expression values.

The TNoM score of a gene is defined as:

$$TNoM(g) = \min_{a,b} Err(a, b | g) \quad (2)$$

and defines the number of errors made by the best rule. The intuition is that this number reflects the quality of decisions made based solely on the expression levels of this gene.

A shortcoming of the TNoM score is that it provides partial information about the quality of the predictions made by the best rule. Thus, for example, TNoM does not distinguish a rule that makes k one-sided errors (e.g., all the errors are tissues of class+that are predicted as −) and a rule that makes k/2 errors of the first kind and k/2 errors of the second kind. This distinction is important, since the rule that makes only one-sided errors performs very inadequately in the cases that are above (or below) the threshold. In such a circumstance, it would be expected that the rule would have less confidence in the predictions it makes on this side of the threshold.

To make finer distinctions, measurements of the sample label information provided by a thresholded gene expression vector are performed. For this purpose the information-theoretic notion of mutual information is employed. Defining X and Y as two random variables, and setting P(X, Y) as their joint distribution, the mutual information between X and Y is defined as:

$$I(X;Y)=H(Y)-H(Y|X) \quad (3)$$

where H(Y)=E[−log P(Y)] and H(Y I X)=E[−log P(Y I X)] are the entropy and conditional entropy of Y given X, respectively. As an example, mutual information can be interpreted as the number of bits saved in compressing values of Y if both the sender and the receiver of the compressed message know the value of X.

In the present invention, the mutual information is measured between labels and expression values using the empirical distribution induced by g and a threshold as follows:

For α ∈{−1,+1} and any b set, $$t_{a,b}(x)=\text{sign}(ax+b) \quad (4)$$

To appropriate this to variables l and x, let M(l,x) be the number of samples in D in which $l_i$=l and $t_{a,b}(x[g])$=x. The empirical distribution is defined as $P_{D,g}(l,x)$=M(l,x)/m. This defines two jointly distributed random variables L and $X_{g,a,b}$. To evaluate choices of a and b, the mutual information for these variables is computed.

The conditional entropy term H(L I $X_{g,a,b}$) is used for comparing different genes and thresholds, since the entropy term H(L) is the same for all genes being compared. Thus, to provide the most informative threshold of a gene g it is desired to find the parameters that minimize H(L I $X_{g,a,b}$), as follows:

$$\text{Info}(g) = \min_{a,b} H(l \mid X_{g,a,b}) \quad (5)$$

As with the TNoM score, the information score of a gene is found by exhaustively searching over all possible 2(m+1) linear decision rules.

The information score may be alternately derived as follows: supposing one wishes to predict a label, given the expression value of g. One way to do this is to estimate the probability of labels given the expression level of g. That is, seek a function $f(l \mid x)$ that represents an estimate of $P(L=1 \mid X_g = x)$, where L denotes the sample label and Xg the expression level of gene g, Generally, a parametric family of functions is determined. The vector parameterization is realized by denoting the family member determined by θ as $f(l \mid x: \theta)$. To evaluate and compare different parameter settings we define the log loss function:

$$ll(\theta \mid L, X_g) = \frac{1}{m} \sum -\log f(l_i \mid x_i[g] : \theta) \quad (6)$$

The term $-ll(\theta \mid L, X_g)$ is the logarithm of the probability of obtaining the observed labeling on the measured $X_g$ according to the model dictated by θ. Thus, minimizing the log loss function is equivalent to maximizing the likelihood of θ.

The choice of the parametric family determines the type of predictions that can be made. One simple family of predictors employs linear thresholds:

$$f_t(+ \mid x: a, b, p, q) = \begin{cases} p \ \text{sign}(ax+b) = + \\ q \ \text{sign}(ax+b) = - \end{cases} \quad (7)$$

$$\text{and } f_t(- \mid x: a, b, p, q) = 1 - f_t(+ \mid x: a, b, p, q). \quad (8)$$

This predictor uses one coin (p) for labels when x is above the threshold, and another coin (q) when x is below the threshold. For this parameterized family, the log loss function is related to the conditional entropy.

If the parameterized family $f_t(1 \mid x: a, b, p, q)$ is used, then $$H(L \mid X_{g,a,b}) = \min_{a,b} ll(a, b, p, q : L, X_g) \quad (9)$$

and consequently, $$\text{Info}(g) = \min_{a,b,p,q} ll(a,b,p,q \mid L, X_g) \quad (10)$$

When analyzing actual gene expression data, many genes may be encountered which are strongly indicative of the class of the samples. One way to evaluate the significance of such strength is to test the results against random data. More explicitly, it is desired to estimate the probability of a gene scoring better than some fixed level s in randomly labeled data. The resulting value of the estimate is known as the p-value corresponding to the scoring method in effect and the given level s. Genes with very low p-values are very rare in random data and the relevance of such genes to the studied phenomenon is therefore likely to have biological, mechanistic or protocol reasons. Genes with low p-values for which mechanistic and protocol reasons can be ruled out are interesting subjects for further investigation and are expected to give deeper insight into the phenomenon being studied.

To determine p-values, let $\{-,+\}^{(n,p)}$ denote all vectors with n '−' entries and p '+' entries (the normal/cancer semantic is one possible interpretation). Let u be a vector of labels, and let g be a vector of gene expression values. A scoring method S (e.g., TNoM or Info) is a function that takes g and u and returns the score of g with respect to labeling u.

Let $U_{n,p}$ be a random vector drawn uniformly over $\{-,+\}^{(n,p)}$. The p-value of a score level s is then:

$$pVal(s:g,n,p) = Prob(S(g, U_{n,p}) \leq s) \quad (11)$$

Note that since $U_{n,p}$ is uniformly drawn, the order of expression values in g does not change the p-value of the scores. Thus, it can be assumed, without loss of generality, that the values in g appear in ascending order. Furthermore, note that both the TNoM score and the Info score are insensitive to the actual distance between consecutive expression values of the gene. Thus, when the p-values of these scores are examined, there is no need to examine the specifics of g.

The combinatorial character of TNoM makes it amenable to rigorous calculations. Ben-Dor et al., "Tissue Classification with Gene Expression Profiles", J. Computational Biology, 2000, which is incorporated herein in its entirety by reference thereto, developed a recursive procedure that computes the exact distribution of TNoM scores in $\{-,+\}^{(n,p)}$. The procedure estimates the number of permutations in $\{-,+\}^{(n,p)}$ for which the TnoM score is exactly k. This is then developed into a recursive formula that involves the number of labels in $\{-,+\}^{(n-1,p)}$ and $\{-,+\}^{(n,p-1)}$ with TNoM score k and k−1.

The analysis of Ben-Dor et al. in "Tissue Classification with Gene Expression Profiles", J. Computational Biology, 2000, does not directly extend for computing p-values for other scores, such as the Info score, for example. An alternative approach yields exact values for inferring p-values. This approach is described in Ben Dor et al., "Class Discovery in Gene Expression Data", Fifth Annual International Conference on Computational Molecular Biology", 2001, and is based upon a dynamic programming procedure to directly compute the p-values. Ben Dor et al., "Class Discovery in Gene Expression Data", Fifth Annual International Conference on Computational Molecular Biology", 2001 is hereby incorporated herein, in its entirety, by reference thereto.

A seemingly simple alternative is to use stochastic simulations for evaluating p-values. Such a procedure generates random samples from $\{-,+\}^{(n,p)}$, and computes the score of each sampled labeling. Then an estimate of the p-value of s can be made by computing the fraction of samples with scores smaller than s. Simple stochastic simulation procedures suffer from a drawback, since in order to compute the p-value of a rare score, a very large number of samples must be generated. Since the identification of rare genes is the focus of the investigation, this makes simple stochastic sampling impractical for such a focus.

Focusing the sampling on the interesting parts of $\{-,+\}$ (n,p) may potentially overcome the afore-stated drawback. Such focus may be achieved based upon the intuiting that a reasonably good division of negative and positive labels above and below a given threshold value exists in a labeling vector u that has a small TNoM score. Thus such u is expected to score well with other methods as well. Sampling from the rare TNoM scores therefore enriches the occurrence of well-scoring vectors. To formalize this the p0 value term is rewritten as:

$$Prob(S(U_n,p)::;s) = LPr_tob(S(U_n,p)::;slAt) \cdot Prob(At) \quad (12)$$

where At denotes [TnoM(Un,p)=t, from which Prob(At) can be computed.

Vectors from At are uniformly sample from At, and then the fraction of samples with scores less than or equal to s are computed to estimate Prob(S(Un,p)~slAt) for different values of t. These estimated conditional probabilities for different values of t are combined using equation (12) to get an approximation of the p-values. Sampling from At is done recursively in a manner that follows the general lines of the recursive process for the calculation of the size of sets in $\{-,+\}(n,p)$ with particular TnoM score.

Further, smooth scoring methods may be employed, including Logistic Prediction and Gaussian Separation Score. It is desirable that expression values close to the decision threshold have both probability label values close to ½. On the other hand, there should be confidence in prediction values for extreme expression values, e.g., the conditional probability is either one or zero. One parametric family that allows for representing such conditional probabilities is the logistic family:

$$f \log it(+Ix:a,b) = \log it(ax+b) \quad (13)$$

where log it(z) is the logistic function:

$$\log it(z) = \frac{1}{1+e-z} \quad (14)$$

In the logistic family, the probability of + is a sigmoid function that asymptotes to zero and one at the extreme values of z. The value −b/a determines the point at which the probability of both labels is equal. The sign of the a parameter determined whether higher expression values are assigned higher probability of + or −. The magnitude of a determines the slope at the threshold point. Thus a larger value of a implies a narrower region of uncertainty about the label.

To score a gene the method requires finding the parameters a and b that minimize the log loss function. Gradient based non-linear optimization may be employed for this task. Although there is no analytic solution for the best parameters, the gradient of the log loss function can be efficiently computed with respect to a and b, using conjugate gradient descent methods to optimize the parameters.

Regarding Gaussian Separation Scoring, the intuition is that the separation between two groups of expression values is proportional to distance between their means. However, the distance has to be normalized by the standard deviation of the groups. A large standard deviation implies an expectation to find points in the group that are far away from the mean value and thus the separation would not be strong. Gaussian Separation Scoring is expected to work well when the data tends toward normal distribution in each class of samples. In such a case, the estimate of the standard deviation takes into account all data points that are presented. On the other hand, if the data is not close to being normally distributed, this score may not be appropriate. For example, an asymmetric distribution of values in one of the classes can skew the estimation of the variance resulting in a misleading score.

When working with actual gene expression data, it is often the case that expression levels for some genes are not reported for some samples, due to measurement problems or some other anomaly. The result is that the mixture of labels that need to be considered is dependent upon the gene in question. For example, a TNoM score of zero has a different meaning for and n+20 and p=20 mixture than it does for a mixture of n=20 and p=5. When selecting a subset of genes as a classification platform or when looking for insight into the studied biological process, consideration should therefore be taken of the relevance of each gene in the context of the appropriate mixture. Absolute score values do not provide a uniform figure of merit in this context. P-values are used as a uniform platform for such comparisons, as they do depend upon the mixture that defines the model, and thus emphasizes the importance of statistical benchmarking of relevance scores.

Additionally, hypergeometric methods may be employed for identifying rare values. For example, assume that a ranking of genes is given as: $g_1, g_2, \ldots, g_M$, and that this ranking is the result of some measurement performed on this given set of genes, such as: differences in copy number changes between two cancer subtypes or differences in expression level. For example, when ranking according to differences in copy number changes between two cancer subtypes, genes may be ranked high if a sharp difference comparing copy number changes in cells from "Type A cancer" with copy number changes in cells from "Type B cancer" is measured. Such measurements can be implemented using cDNA CGH techniques.

When ranking according to differences in expression level, for example, genes may be ranked high if a sharp difference is measure in comparing expression levels in cells from "Type A cancer" with those from "Type B cancer". These measurements can be implemented using microarrays.

Hypergeometric statistics may be implements for statistical assessment of the correlation between the given ranking or order and chromosomal location of the gene being ranked, with a goal of identifying chromosomal regions that have a statistically significant high representation at the upper part of the ranking order.

The null model for this method assumes no relationship between the phenomenon on which the ranking is based and chromosomal location. The corresponding mathematical model is the hypergeometric model described below.

For a given chromosomal region R (e.g., a cytoband, a sub-band or a range of base indices) and a given order of genes $g_1, g_2, \ldots, g_M$, where the higher ranks are listed first (i.e., $g_1$ being the highest), the vector v is computed as follows: V(i)=1 if $g_i$ is located in R; otherwise v(i)=0. The max-surprise p-value of the density of genes located in R, in the higher ranks, is given by:

$$p = \max_{1 \leq m \leq M} \left\{ 1 - F\left(\sum_{i=1}^{m} v(i) - 1, M, K, m\right) \right\} \quad (14)$$

where

M is the total number of genes,

K is the total number of genes located in R, and

F is the hypergeometric cumulative distribution function given by:

$$F(x, M, K, m) = \frac{\sum_{y=0}^{x} \binom{m}{y}\binom{M-m}{K-y}}{\binom{M}{K}} \quad (15)$$

The hypergeometric distribution function represents the probability that in drawing objects without replacement from a collection of K black objects and M-K white objects, x or less out of the m objects first drawn are black. As applied to chromosomal locations and ranked genes, the null model assumes that there is no relationship between the chromosomal region and the ranking, as noted above. The relationship $$x = \sum_{i=1}^{m} v(i)$$

represents the number of genes located in R amongst the m number of highest ranking genes. The probability of seeing x or more R-located genes in m randomly drawn genes (with reference to the null model) is 1−F(x−1, M, K, m). Maximizing over m give a top cut of the ranking list where the most surprising density of R-located genes is observed.

By representing the relevance scores of the rows of expression levels shown in the visualizations, a user will be able to identify good separators not only by a subjective visual evaluation of the differentials between the color encoding of the expression values of the normal values vs. the tumor values (by viewing the colum-order matrix 200 or matrices 200n, 200t), but a more quantitative indicator can be viewed in the relevance score visualization (indicated by a histogram or line entries in a relevance scoring chart 210 which is visualized adjacent the chromosome map 17 in FIG. 4, but which also may be indicated by color-encoding, or by binary code. For example, if a p-value (relevance score) is calculated to be below a predetermined threshold value, it may be represented with black encoding, while if it is calculated to be above the predetermined threshold value, it may be encoded as white). Ultimately, when a certain density of indicator genes in a location of a chromosome is located, this can be a very useful diagnostic tool in determining where a problem area in a chromosome exists for a particular type of cancer. For example, in the visualization of FIG. 4, the histogram 210 could possibly be indicating that the region of chromosome 17 in which the genes expressed by rows R2, R10 and R8 reside may be a problem area that exists for the type of cancer being examined, as each of these rows displays a relatively high relevance score in the histogram 210.

CGH graphing along the chromosome map can also be accommodated, in the form of bars or column(s) with color codes, for example. The CGH graph is a measure of chromosomal instability or chromosomal aberration and is indicative of copy number change in regions of the DNA (amplification or deletion). This can be indicative of a trigger to cancer in many instances. Two copies of the genetic material (reflecting a pair of chromosomes) is the normal number expected and is graphed as the normal line in a bar or histogram type CGH graph.

Figure 5A:
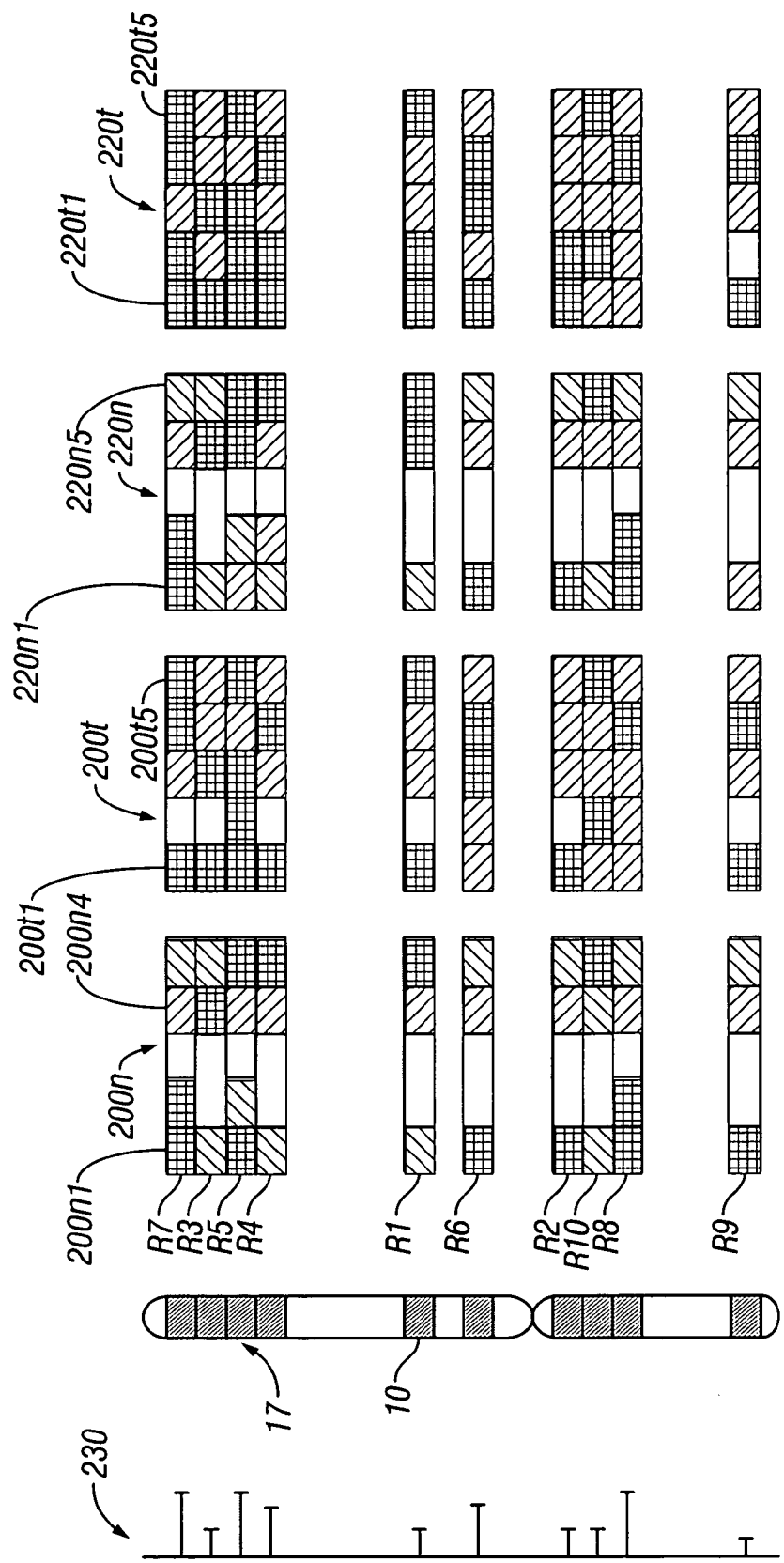
FIG. 5A is a schematic diagram of a visual display in which a pair of matrices of chromosomal copy number abnormality values correspond to the expression matrices of FIG. 4 have been displayed adjacent the expression matrices. Additionally, relevance values of the chromosomal copy number abnormality data are plotted relative to the positions of the genes represented by the chromosomal copy number abnormality data.

In the example shown in FIG. 5A, matrices 220n and 220t are displayed along side matrices 200n and 200t, to display the chromosomal copy number abnormality values for the genes represented by the values in the corresponding rows and columns of the expression matrices 200n, 200t. In the example shown, the chromosomal copy number abnormality values are represented by color-coding, much in the same way that color coding is used in the well-known heat map representations of expression values from a microarray. Alternatively, the chromosomal copy number abnormality values may be represented in histogram or other line style graphical format. It should be noted here, that the display of chromosomal copy number abnormalities aside a chromosome map is not dependent upon the display of expression values, even though the expression values are displayed in the example of FIG. 5A. Chromosomal copy number abnormalities may be displayed along side and mapped to chromosomal locations without displaying expression values, but while displaying other related information, such as annotations, and the like, as described above. The same is true for other display features described above and below, e.g., relevance values can be displayed with or without any of expression values, chromosomal copy number abnormality values, etc.

Like expression values, relevance values of the chromosomal copy number abnormality values for the rows of genes upon which the experiments were performed can be calculated using hypergeometric statistical methods as discussed above, for example, to separate two or more types of tumor cells, or to differentiate between responder and nonresponders. For example, because of chromosomal copy number abnormalities, some patients may not respond to a particular type of treatment, while other patients not having such chromosomal copy number abnormalities, or having a lower chromosomal copy number abnormality value may respond to the same treatment. Upon discovering such a relationship, the present techniques may be used to predict or tailor effective treatments for patients based, at least in part, on chromosomal copy number abnormality data and its localization to regions on the genome. Normal tissues may also be included in these methodologies, but are used mainly for calibration purposes. By scoring the relevance of each row, relevance scores can be graphed in a similar manner to that described above with regard to relevance scoring of the expression values. Thus, each of the rows of CGH (chromosomal copy number abnormality) values can be reduced to a representation of the relevance or difference scores, taken from the entire set of measurements. Because the normal tissues generally score very low for chromosomal copy number abnormality by definition, they may be used for reference values. The tumor tissues may have various scores for chromosomal copy number abnormality, and clusters having different values may be apparent, which may be used for classification or separation of the tissues, and for localizing differences to genomic regions. The CGH values can be used to determine which areas in the chromosomes are amplified or deleted. By identification of characteristic genes and characteristic gene data, a relationship among areas of a chromosome and the pathogenesis of a cancer can be established regardless of what the expression data is indicating.

For example, in order to provide relevance scoring of the chromosomal copy number abnormality data in FIG. 5A, each row of values in the matrices 220n and 220t may be scored for relevance, and the relevance values are then plotted on a separate visualization, such as histogram 230. For example, such hypergeometric statistical methods may be employed to infer the density of chromosomal copy number abnormalities in a chromosomal location, such as plotted in the histogram of FIG. 6C, or other available statistical methods may be employed. A user can visually identify likely indicators of cancer-related genes based on CGH (chromosomal copy number abnormality) data by reviewing the relevance scores in visualization 230, as well as by analyzing trends within the matrix data 220*n*, 220*t*.

Figure 5B:
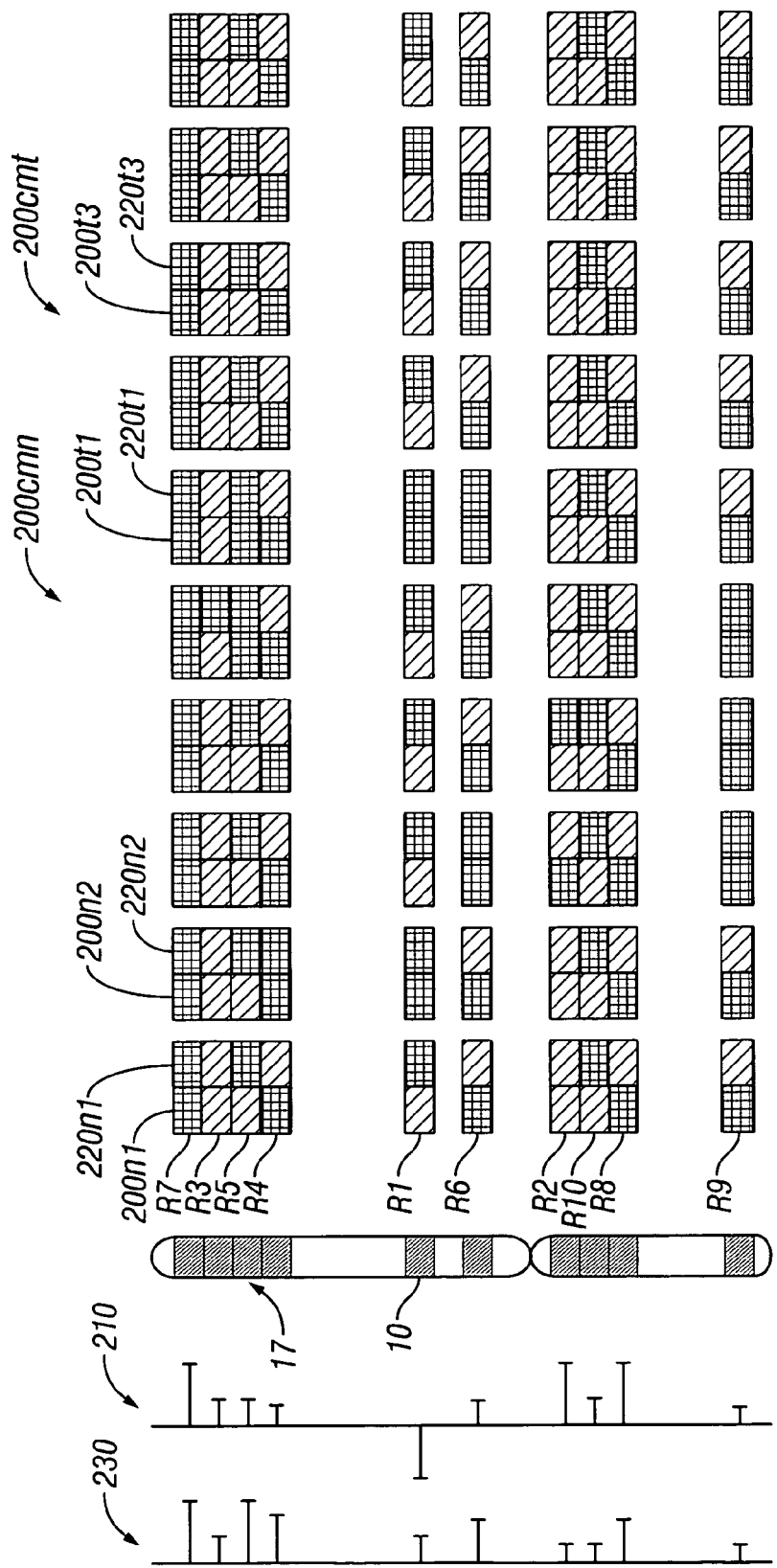
FIG. 5B is a schematic diagram of a visual display in which the chromosomal copy number abnormality matrices in FIG. 5A have been interlaced with the expression matrices of FIG. 5B. Additionally, relevance values of the chromosomal copy number abnormality data are plotted relative to the positions of the genes represented by the chromosomal copy number abnormality data, and relevance values of the expression data are also plotted.

A more current technique for CGH measurement analyzes arrays and derives a microarray format of chromosomal copy number abnormality values. By using this data the present invention displays a composite matrix 200*cmn*, 200*cmt* for different clusters or classes of tumor experiments (FIG. 5B) in which a column of chromosomal copy number abnormality data is positioned adjacent each column of expression data that it characterizes (see 200*n*1, 220*n*1; 200*n*2, 220*n*2; 200*t*1, 220*t*1; 200*t*3, 220*t*3; etc). The chromosomal copy number abnormality data may be expressed with color-encoding, like a heat map, so that differentiation between deletion and amplification can be readily visually identified. Similarly, this differentiation can be expressed in a line map by directionality, wherein lines indicating deletion are drawn in one direction and lines indicating amplification are drawn in the opposite direction.

Figure 6A:
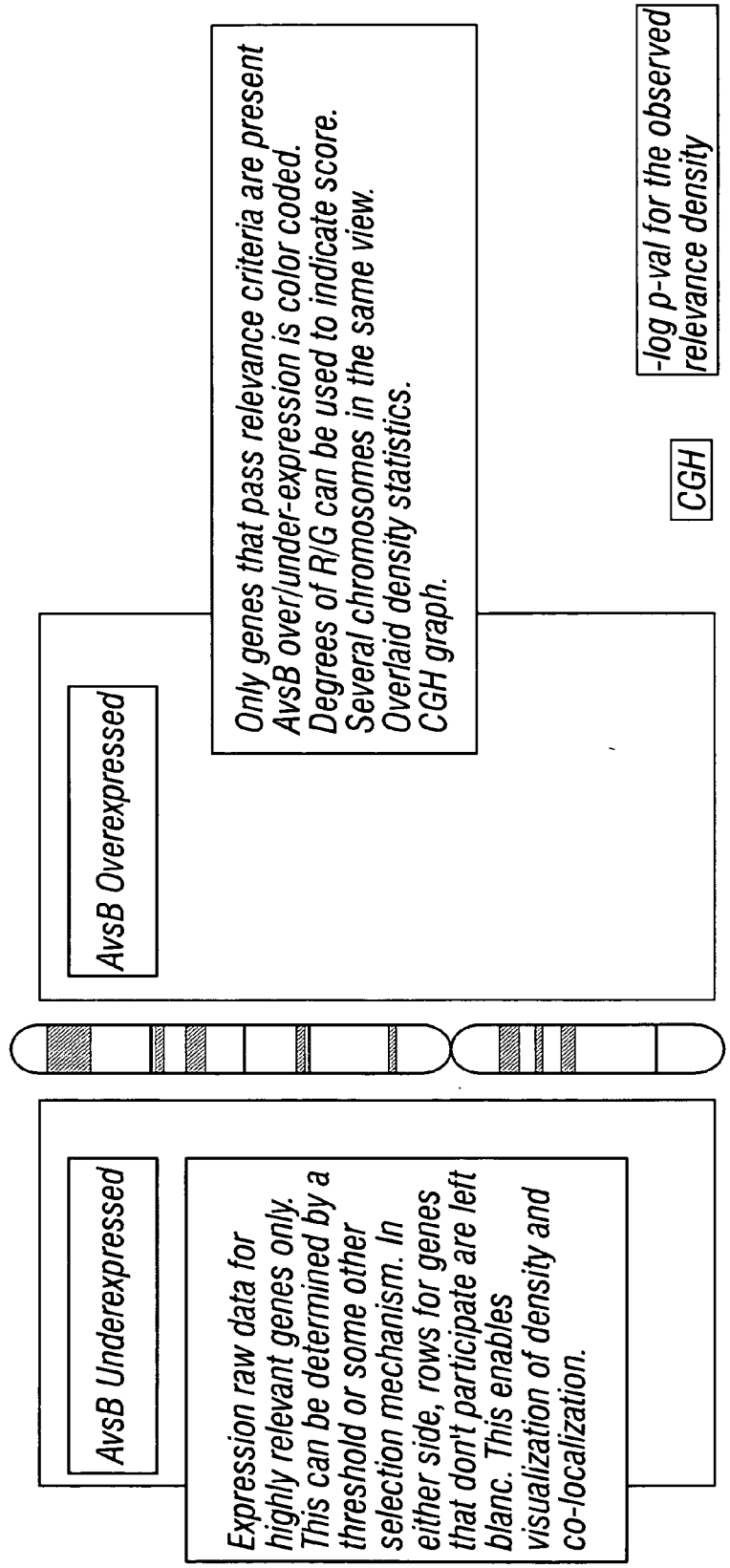
FIG. 6A is a schematic representation showing heatmap visualizations of expression levels of genes that sharply separate samples from two classes. The heat map visualizations are mapped to the locations of the genes (on a chromosome map) from which the expression levels originated.

To further reduce the complexity of the information that is being viewed, the present invention provides for a type of filtering mechanism in which only those expression values or chromosomal aberration values that meet or exceed certain relevance criteria are displayed. For example, FIG. 6A shows a case where a minimum level for over-expression (e.g., red values) is set and a maximum level for under-expression (e.g., green values) is set. In this case, only those expression levels which are greater than or equal to the maximum level of over-expression, or less than or equal to the maximum level of under-expression are depicted. Two matrices are generated, one 240 for the under-expressed values passing the relevance criteria and the other 250 for the over-expressed values passing the criteria. In either side (i.e., either matrix 240 or matrix 250), rows for genes that don't participate are left blank. This enables visualization of density and co-localization.

The rows that do pass the relevance criteria and are displayed in matrices 240, 250 may be color-coded in the same fashion that expression levels are color coded in a conventional heat map, where degrees or shade of coloration may be used to indicate variations in scores. Several chromosome maps annotated in this fashion may be displayed on the same user interface. Additionally, overlaid density statistics, as described above and/or other annotations such as GO annotations may be displayed and/or chromosomal copy number abnormality views may be displayed. A display such as shown in FIG. 6A shows relevance of the expression values more clearly and allows the user to more easily identify relevance density among the data.

Figure 6C:
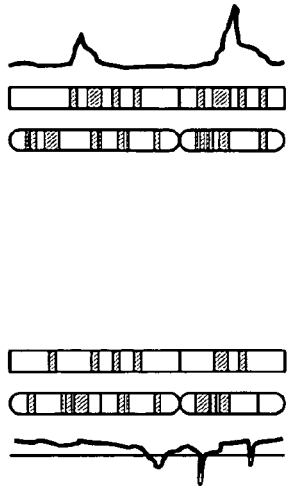
FIGS. 6B-6C show "p-value" plots relative to chromosomal location, for observing class separation between the two classes of samples represented in FIG. 6A, or for observing CGH separation for those classes. Also shown is a plot of other information (e.g.: CGH information where the p-values are expression derived, presence of motifs in the regulatory regions, regulation related information, etc.)
Figure 6B:
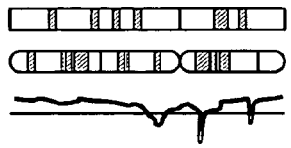

FIG. 6B shows a visualization in which the matrix 200 has been converted only to relevance scores. The rectangular display on the right side of the fig. displays cluster membership of the data, in a manner as described above. The histogram to the left of the chromosome display maps CGH values.

FIG. 6C shows another variation in which selections are made according to cluster membership. Cluster membership can be inferred from a cluster analysis performed on the data. Then an additional bar (the rectangular bar that forms the central portion of FIG. 6C) can use colors to indicate membership in functional clusters localized to the genome. For example, genes in a first cluster may be indicated by a red bar, genes in a second cluster may be indicated by a green bar, genes in third cluster may be indicated by a blue bar, etc. The histogram to the right of the rectangular cluster display indicates relevance density.

Figure 7A:
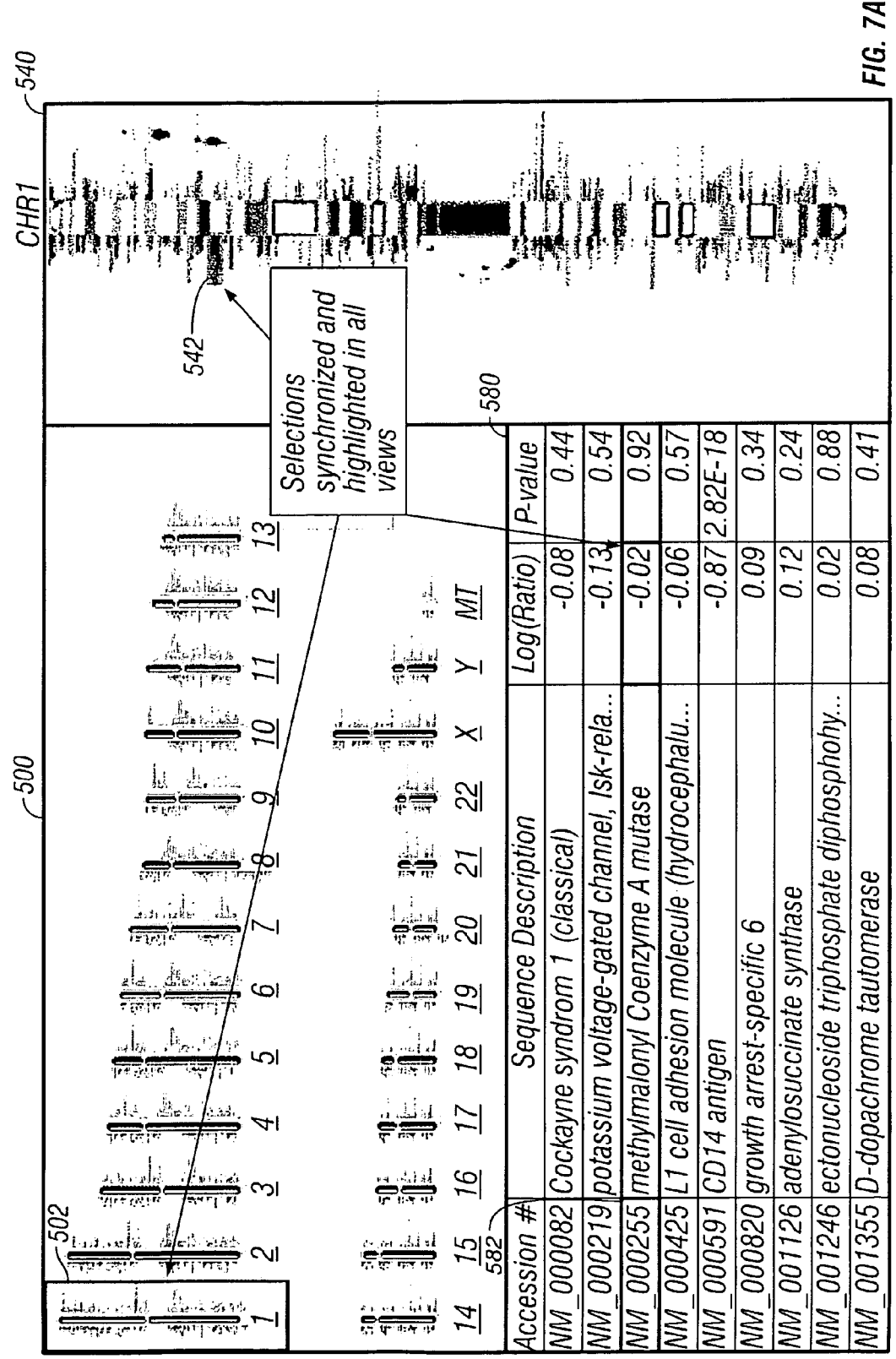
FIG. 7A shows a display of a composite visualization according to the present invention which takes advantage of zooming capabilities to provide differing level views of the mapping information.
Figure 7B:
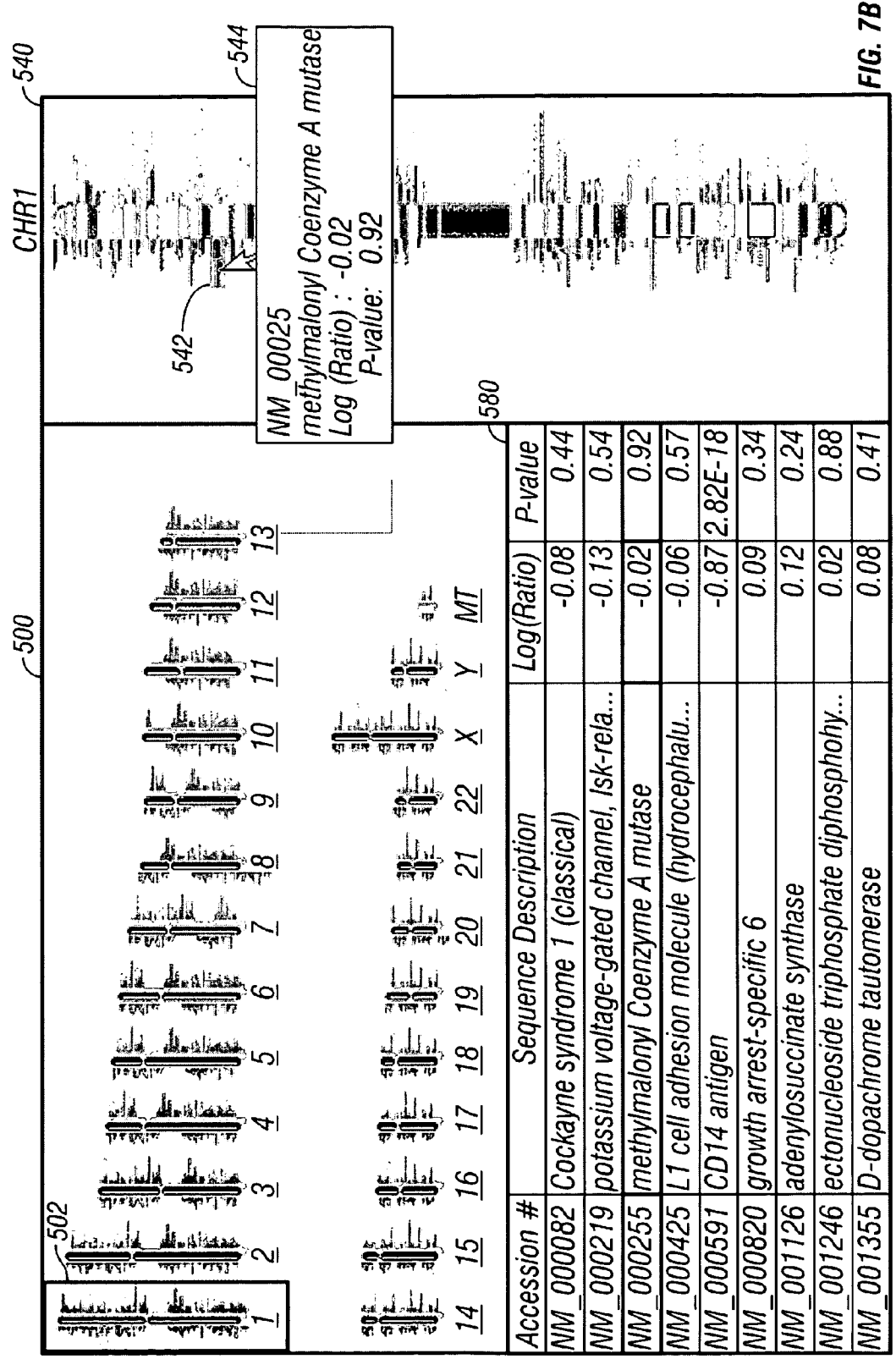
FIG. 7B shows the display of FIG. 7A, in addition to a tooltip feature which has been invoked to display additional details about the selected item.

Referring now to FIGS. 7A-7B, a display is shown which takes advantage of zooming capabilities to provide differing level views of the mapping information. For example, high level, medium level and detailed views may be provided on the same interface without having to do any context switching. A first view 500 shows a high level view of the mapping, which, in this instance is a full genome view. However, it is noted that the high level view is not to be limited to a full genome view, as a select grouping of chromosome maps (or even one chromosome map) and related visualizations could be shown here. By selecting one of the chromosomes in the high level viewer 500 with a cursor mechanism (chromosome 1 is selected in FIG. 7) a mid-level view 540 of the selected chromosome appears in viewer 540 to show the map in greater detail. An indicator such as box 502 indicates the selection of the map portion to be magnified in the mid-level view. It is also possible to select more than one chromosome map for amplification in the mid level view, although the amplification will be less than the case when only one chromosome map is selected, and, although possible, it is generally the case that a researcher will be more interested in studying and making comparisons among genes within a single chromosome. Optionally, the selected portion of the high level view may be highlighted to further emphasize what is being zoomed in on in the mid-level view.

A low level or detailed view 580 is further provided to show specific details as to genes and annotations thereof (e.g., regulatory regions, known promoters, etc.). A cursor selection of a particular region in the mid-level viewer 540 determines the specific data which is displayed in viewer 580. All three viewers 500, 540 and 580 are interlinked so that each is updated whenever a manipulation of any of the viewers is performed. In the example shown in FIG. 7B, the accession number NM_000255 has been selected as indicated by the highlighting 582 in the detail view 580. At the same time, a cursor, highlighter or other indicator 542 is placed over the locus of the gene on chromosome 1, which corresponds to the location of the gene identified by accession number NM_000255, in mid-level viewer 540. Optionally, a highlighting feature may be provided to highlight the same location in the high-level viewer 500, but of course, the location will not be accurately identifiable, but only generally identifiable, due to the substantial compression of the information that is required for the high level view. In the high level view, and potentially in the mid-level view, data merging techniques are employed where data would otherwise overlap, due to the compressed view.

Because all viewers are interactively linked, a user can click on any portion of any single viewer of the display and the corresponding features in the other viewers will be automatically and simultaneously selected. In this way a selection of an element in the details table (viewer) 580 can be immediately seen in the context of both the zoomed chromosome view 540 as well as the full genome view 500. The high level viewer allows the investigator to visualize all measurements within the complete context of not only all experimental data, but also in the context of the entire genome. At the same time, one can focus on a specific data element (or group of elements). In this way, the arrangement of FIGS. 7A-7B maintains both focus and context simultaneously. Further details about the provision of viewers for maintaining focus and context and for providing zooming and compression capabilities of visualizations can be found in co-pending commonly owned application Ser. No. 10/209,477, filed Jul. 30, 2002 and titled "Method of Identifying Trends, Correlations and Similarities Among Diverse Biological Data Sets and System for Facilitation Identification" and co-pending, commonly owned application Ser. No. 60/402,566, filed Aug. 8, 2002 and Ser. No. 10/403,762, filed Mar. 31, 2003, each titled "Methods and System for Simultaneous Visualization and Manipulation of Multiple Data Types". application Ser. No. 10/209,477, 60/402,566, and Ser. No. 10/403,762 are all hereby incorporated by reference, in their entireties.

For areas of the display where the information displayed next to the chromosome maps is too dense to display all of it on the pixel space allotted (such as the gene expression data mapped in the full genome view, for example), a compressed view of this data is represented. One example of a compressed view involves displaying only minimum and maximum, or average values of the expression or other data for a given location on the GUI to show the range of values that span multiple locations that have been compressed to the same pixel location on the display by necessity. Additionally, color-coding may be used to help differentiate the display of particularly dense data. For example, positively expressed values can be displayed in one color (e.g., blue) while negatively expressed values can be displayed in another contrasting color (e.g., white). Reference is again made to application Ser. Nos 10/209,477 and 60/402,566 for further details and techniques of compressing data for display.

The user interface may be provided with toggling capability to allow a user to quickly toggle through variations in the display of the data, for example to provide toggling between a display of maximum and minimum values, and a display of average values. The user interface may further be provided with query and cuts capabilities, wherein any displayed information that doesn't meet defined structured logical criteria is greyed out, dimmed or removed from the display altogether. Examples of criteria include, for example, all members of a pre-defined list that are differentially expressed by a defined amount; all members of a pre-defined functional family that are differentially expressed, etc. For example, a user may define the system to display only those data that have a p-value of less than one. Further, the user display may be provided with a button, drop-down menu or other interface tool permitting a user to initiate calculation of and/or display relevance scores, relevance densities, annotations, and the like.

Still further additional details about any data item may be made available via tooltips or popup dialogs. For example, by hovering over the highlighted region 542 of view 540, a tooltip 544 may be displayed (FIG. 7B) with additional details about either the measurement or the gene represented by the measurement. As one example, a tooltip overlay 544 is displayed under the gene 542 which has been selected in view 540, as shown in FIG. 7B. For ad hoc browsing of overlay views it is useful to have a lightweight form of "peeking" at the overlay data without disrupting the current selections, which are linked among all views. A further mechanism may distinguish between single clicks to select an overlay element, and a double click, which requests opening up a popup dialog with additional information. A single click, in this arrangement selects an element and simultaneously selects all corresponding elements within the other three views. A double click, in addition to selecting the same information as the single click, also invokes a popup dialog, which displays relevant supplementary details. Such dialog may include more detailed information about the measurement being overlaid (perhaps data that is seldom used and not shown in the standard table view), and/or it may show details about the chromosome location itself, and/or whatever supporting information might be relevant. The supplementary details may come from the dataset being visualized, or it may come from separate supplementary sources such as local genomic databases, external web sites, etc.

Another alternative for accessing supplemental information is by invoking one or more external web pages with information relevant either to the specific accession number in question, or the genetic loci. For instance, a user may invoke the URL for the NCBI LocusLink entry corresponding to the specific expression measurement in question.

Further, the information shown and described with regard to the figures above are only examples of overlaid expression data that can be displayed by the current invention, and the invention is not to be limited to the types of data discussed. Any data suitable for association with a genetic locus could be overlaid in a similar manner, with regard to display of genetic data. The present invention can be used to visualize other classes of data as well, such as proteins, for example. The extension of the user interface to handle CGH, relevance scores, etc. as described above with regard to FIGS. 3A-3C, for example, would be readily apparent to those of ordinary skill in the art after reading the present disclosure.

Lines by chromosome can be expression values (red green values), p-values, CGH values, or the more elaborate view with the matrix, as in the FIG. 2 examples. In high level view, a cursor may be provided to show the user the level of the chromosome at which the detail is showing.

Figure 8:
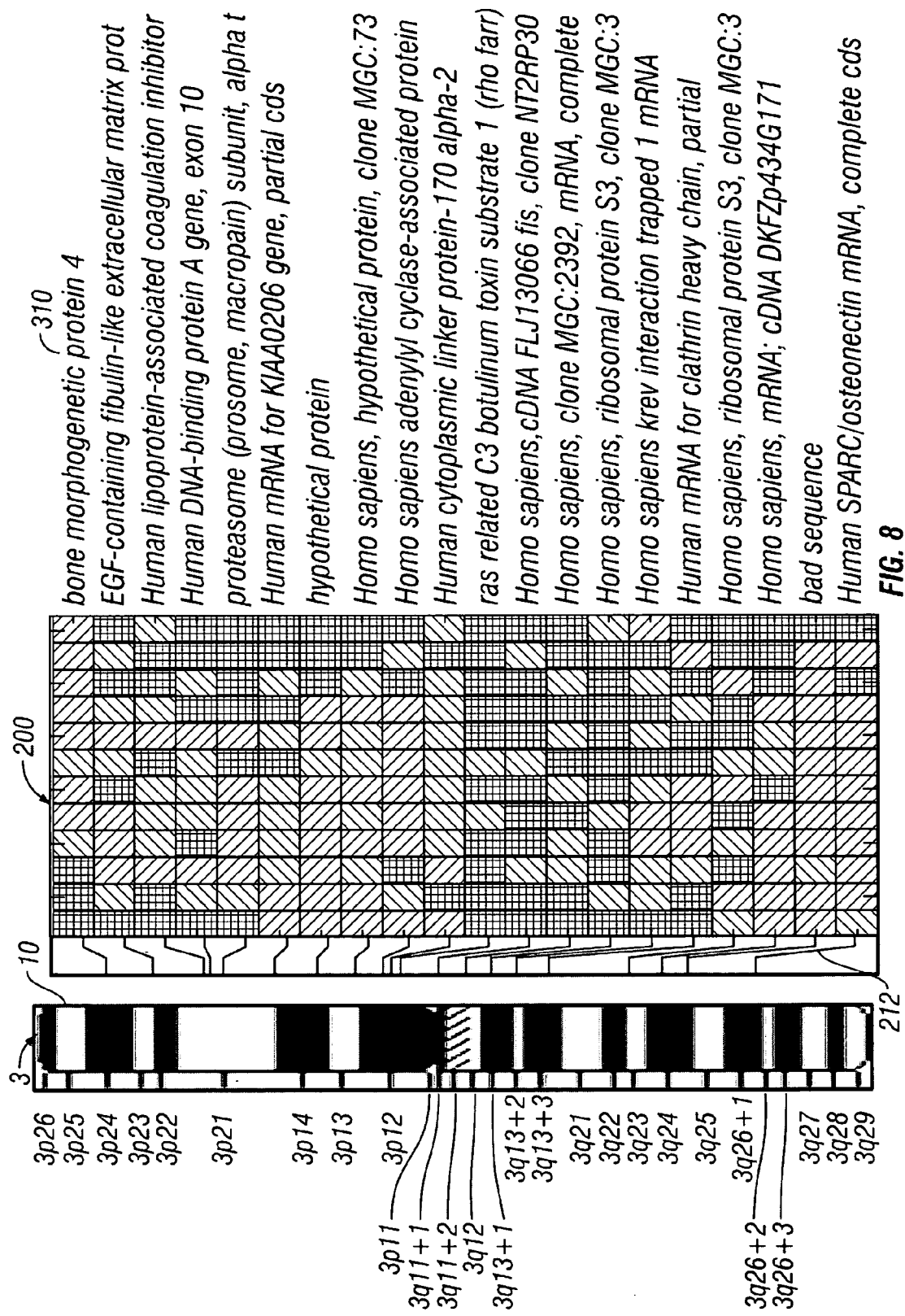
FIG. 8 shows another example of a single chromosome mapping display in which multi-array gene expression data is displayed, wherein the rows of the heat map have been reordered to correspond to their sequential positioning vis a vis the chromosome map, but the rows have not been spatially reordered.

FIG. 8 shows another example of a single chromosome mapping display in which multi-array gene expression data are presented in heat map 200 mapped to the genomic positions on the chromosome 3 which the expression data are related to. Each column of pixels of the (red-green or blue-yellow, for example) heat map 200 represents a different sample or expression array. In this way multiple arrays of data can be observed simultaneously. The ordering of the samples from left to right may be adjustable. For example it may be in the chronological order of the experiments or an order determined by classification or by clustering or by some type of sorting. If hierarchical clustering is being presented, then a hierarchical tree (not shown) may be shown above or below the heat map 200. Annotation 310 related to the genes, messages, or probes (of course, there may be multiple probes per gene) is shown adjacent to the heat map 200. In this example, the heat map 200 is of maximal scale with elements uniformly spaced in the vertical direction. That is, the rows of the heat map have been reordered to correspond to their sequential positioning vis a vis the chromosome map, the same as in the examples described above. However, in this example, the rows have not been spatially reordered, but are all of equal distance with respect to adjacent rows. Rather, mapping lines 212 are overlaid to show the location of the genes on the chromosome as they relate to the expression data in heat map 200. This method of mapping is suitable for a finite number of genes, where the mapping lines may be displayed to be clearly visibly discernable.

This view may likewise be scaleable and zoomable by the user. In this way the user could choose (either by right-click selection of a zoom scale, or by mouse-dragging a rectangle over a specified zoom range) to view the location information at any scale, from a single gene at a time to all chromosomes simultaneously in a single view.

Figure 9:
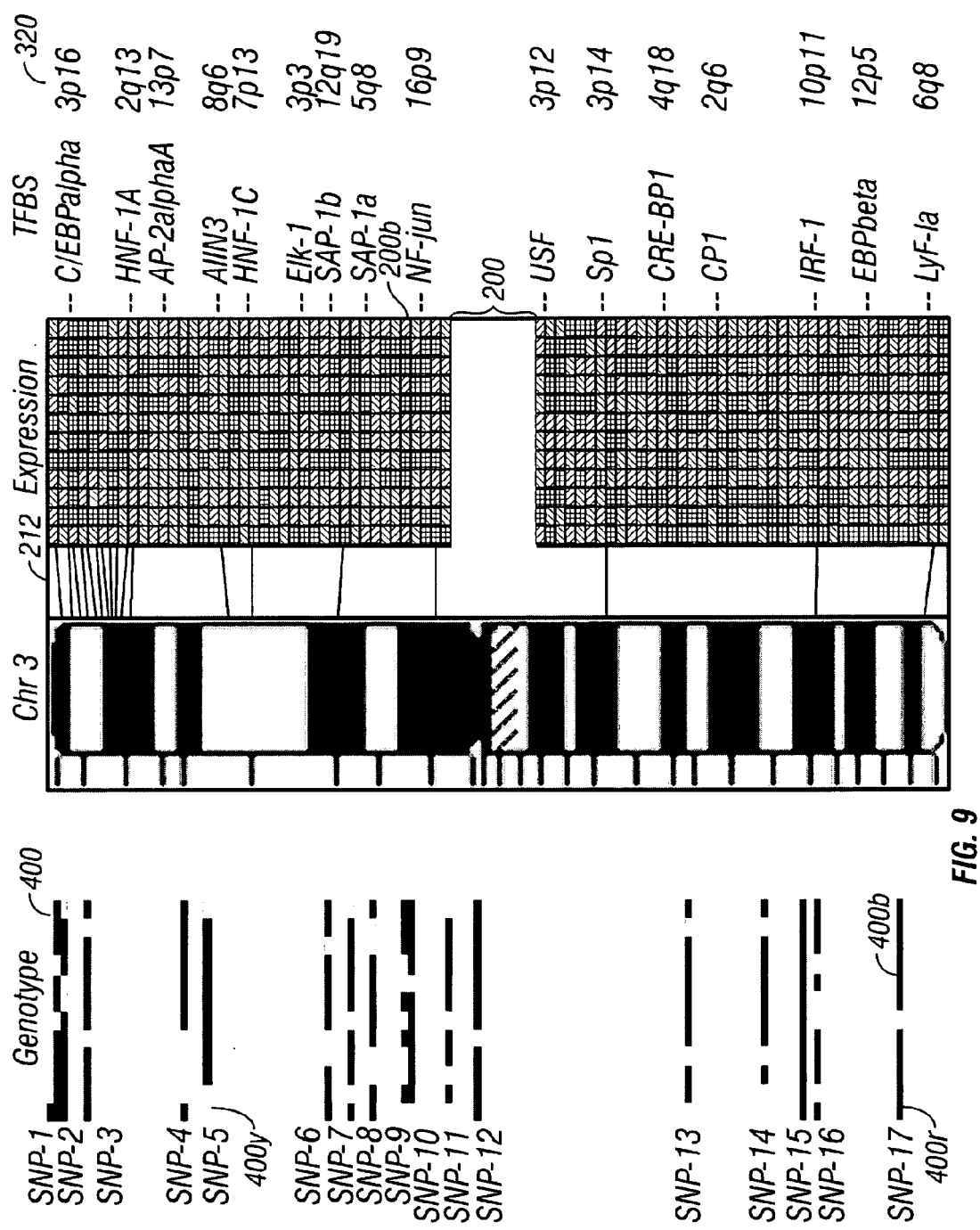
FIG. 9 shows another example of a chromosome mapping display in which a scatter plot of calculated data points is displayed adjacent each chromosome map.

FIG. 9 shows another example of a chromosome mapping display in which all of the chromosomes of an organism are displayed, with the capability of showing at least one chromosome (e.g., chromosome 12 in the example shown) in a magnified, or zoomed view. The example of FIG. 9 shows application to a single microarray or experiment. Ratios of gene expression data (differential expression) or alternatively, straight gene expression data which has not been compared to reference values are calculated and plotted at the corresponding chromosome locations where the genes from which the data was derived from are located. In the example shown, ratios are calculated between a test sample and a reference sample, although this embodiment is not limited to two experiments or sets of data, but can incorporate more sets. Similarly, more than one set of straight gene expression data may be accommodated.

In contrast to those displays previously described, this example displays a scatter plot 350 of the calculated data points (e.g., expression ratios) rather than a bar, histogram or chart-like representation. This plotting of data points tends to separate the data more clearly and make it more readily observable and readable by a user. The data points may be color-coded, such that points to the left of line "0" are color-coded green 352, points to the right of the zero line may be color-coded red 354, and points near zero may be color-coded black 356.

The smaller views of the scatter plots 350, adjacent the chromosomes which are not magnified, may not show the vertical value bars to avoid obscuring this condensed view. Line 358 plots a moving average of the points displayed. An inverted histogram 360 may optionally be displayed at the top of the plot to show the distribution of data points with regard to the associated chromosome 12. Thus, the histogram provides a visual representation of the data point distribution which may provide the user with an easier visualization, or at least an alternative visualization of the data.

Cytogenic staining bands 362 may be displayed on all chromosomes to show the locations of the genes associated with the plotted data points. Standard labeling (e.g., p13.32, q24.32, etc., not shown) may be provided adjacent the locations of the cytogenic staining bands as identifiers to those skilled in reading chromosome maps. Indicators such as horizontally disposed hash marks 364 may be provided to indicate where the microarray probes exist with respect to the associated chromosome, and therefore where data is expected to be displayed. The system provides controls for "turning off" or not displaying those indicators 364 or classes of probes 364 identified by positive, negative or relatively unchanged ratios. Thus, for example, indicators for relatively neutral data may be suppressed while displaying only negatively and positively biased ratio values. The system also provides for suppressing the display of the data points, so that the trend lines (e.g., histogram, moving average) may be more clearly observed. In these situations, indicators 364 aid the visualization to show where those data points would be displayed, if not suppressed.

The textual representation of the data 366 is shown rotated in FIG. 9 to meet the drawing requirements imposed for patent applications. In reality, the textual representation of the data 366 is displayed in the same orientation as the reference numerals for the remainder of the visualization shown in FIG. 9, typically below the graphical representation, and contains a great deal more of textual data.

Figure 10:
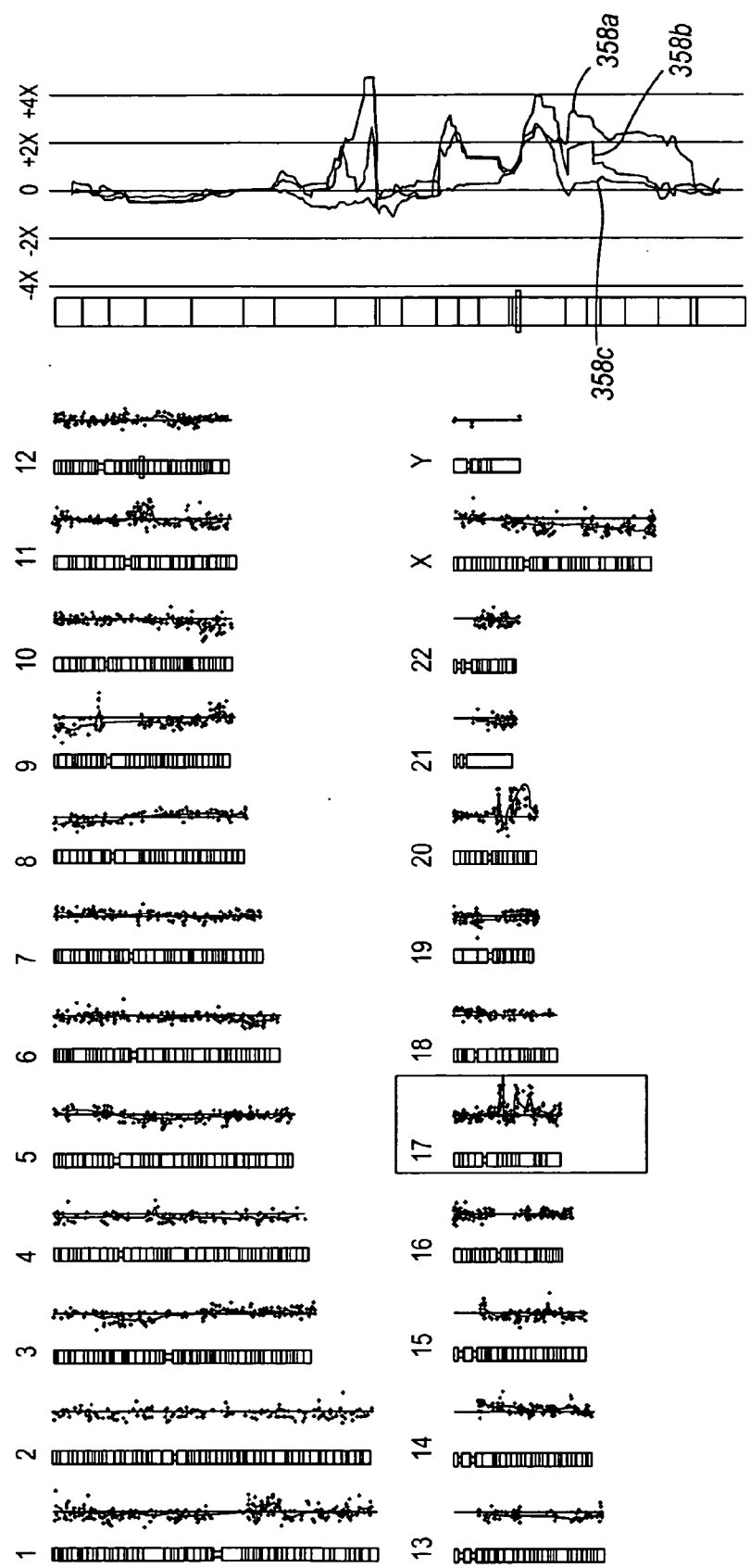
FIG. 10 shows a chromosome mapping display similar to that shown in FIG. 9, but in which multiple experiments have been mapped and displayed.

FIG. 10 shows a chromosome mapping display similar to that of FIG. 9, but showing the additional capability of the system to display multiple experiments simultaneously, as noted by the multiple moving average lines 358a, 358b, 358c plotted adjacent each chromosome representation. Note that the optional histogram has not been displayed in this view. Also, the data points 352, 354 and 356, as well as hash marks 364 are not displayed in this view so as not to overload the representation which may make it overly cumbersome for the viewer to read. However, the system provides the user the ability to optionally display any and all of these features upon the user's selection. Thus, for example, the user may choose to display selections or all of the data points 352, 354, 356 from the experiment described by line 358a. Alternatively, the user may wish to display data points 352, 354, 356 or a subset of the same, from all experiments (i.e., those represented by lines 358a, 358b and 358c in this example). In such an instance, data points from each experiment may be distinguished by color coding. Note that these are only two examples, and that the system is completely flexible with regard to the amount and detail that the user wishes to display. It is further noted that the display of textual data has been omitted from FIG. 10 for purposes of simplifying the drawing.

Increasingly, biologists analyze gene expression data in conjunction with other kinds of data for the same sample, specimen or source. When interpreting the biological implications of the data, it is useful for the biologist to simultaneously view those data of disparate types before making biological hypotheses or drawing conclusions. Consider the case where one or more genes are being silenced. The function of a gene can be effectively knocked out by one or more mechanisms. These include (but are not limited to) inhibition of gene transcription by transcription factors or histone modification, methylation of the DNA sequence within or around the gene, alteration of a gene's sequence by mutations or polymorphisms, alternative exon splicing, and post-translational modifications of the protein product. Many of these effects can be measured by independent experiments that complement the gene expression data from DNA microarrays. While few of these measurements can be made today using high-throughput techniques, the throughputs of such methods are constantly improving.

Transcription factors are classes of molecules that regulate the expression of genes. Transcription factors include both activators and repressors, which respectively up-regulate or down-regulate gene expression. Their DNA binding sites lie in or near the regulated gene(s). Although currently the databases for these sites are incomplete, this information is being collected at a substantial rate. In the near future, it will be increasingly possible to measure the states of these transcription factors and identify the genes affected by each site, when interpreting expression data. In the example shown in FIG. 11, pertinent transcription factor annotation for binding sites and the expression of the genes downstream of them along the genomic sequence is overlaid on the chromosome map, along with mapping of expression data as described previously.

In this example, chromosome 3 is centrally displayed with cytobands 10. In this example, twelve samples (indicated by the 12 columns of array data in matrix 200) are displayed. The gene expression data for all probes for the twelve samples are shown in genomic order in matrix 200. Additionally, polymorphism measurements (or genotypic data) are displayed at 400, and are color-coded where the colors 400y, 400r, 400b (yellow, red and blue, as an example) indicate the presence of alleles, e.g. homozygous wild-type, heterozygous, and homozygous in the variant type.

Figure 11:
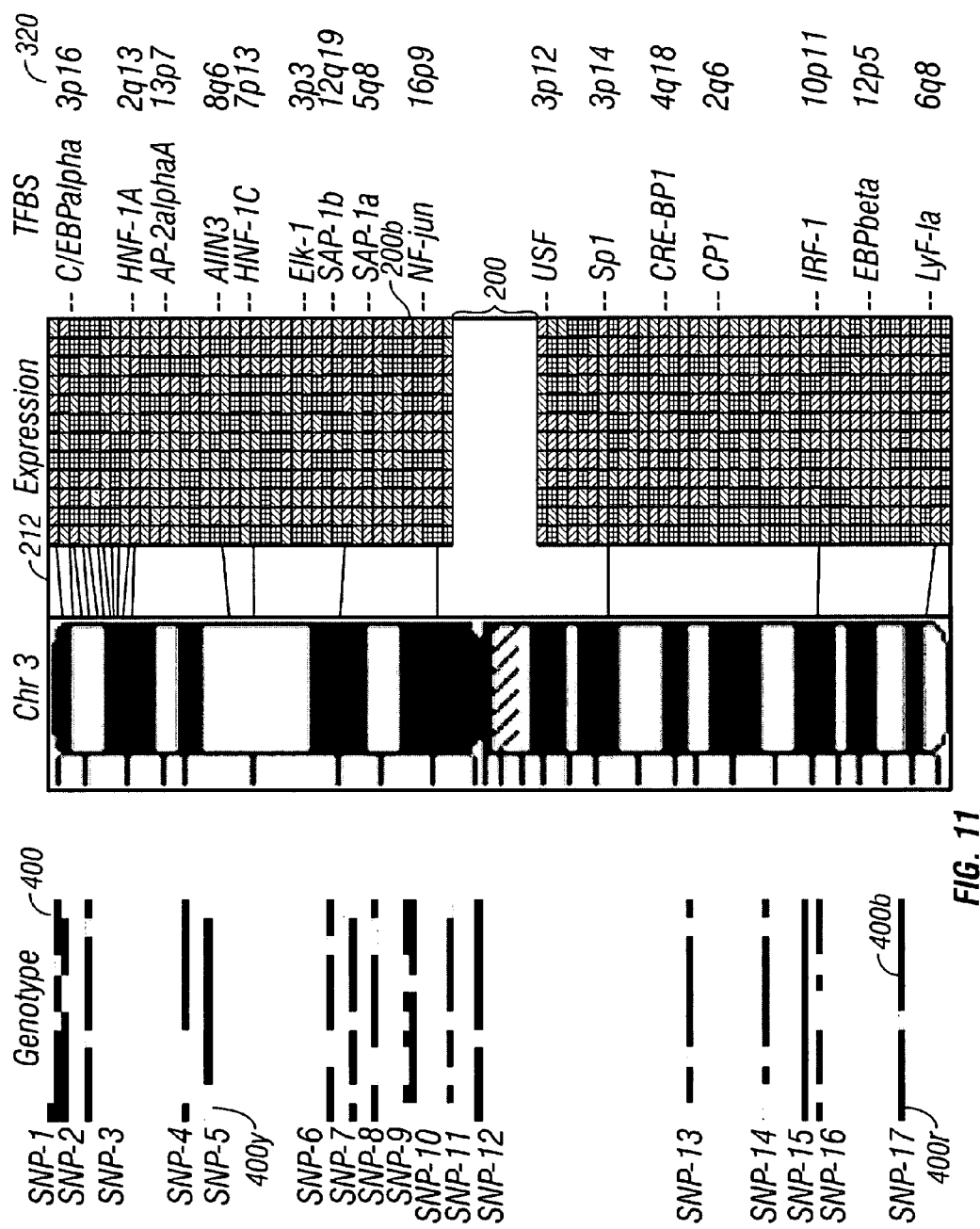
FIG. 11 shows another example of a single chromosome mapping display in which multi-array gene expression data is displayed, in addition to other data such as genotype, transcription factor binding sites and RNA expression for the proteins that bind to each of the transcription factor binding sites.

As shown, the expression map image 200 has elements that are evenly spaced vertically, like the example of FIG. 8. Since the locations of the genes that the expression data represent are not evenly spaced on the chromosome map 3, mapping lines 212 are drawn to indicate the actual positions of the genes as they relate to the positions of the expression data representing the genes. Additional annotation 310 for each of the genes, probes or messages may also be displayed for some reasonable number of expressed probes (as noted above with regard to FIG. 8). Also shown are the positions of transcription factor binding sites 320. Additionally, the expression levels of the transcription factors that are also on the array 200 may be displayed, even if those genes reside on a genomic position far from the region where they bind or on a different chromosome. This information is useful in determining whether that transcription factor may be involved in regulating the expression of a gene or set of genes. The RNA expression for the proteins that bind to each of the transcription factor binding sites is also represented in FIG. 11, shown highlighted within blue rectangular boxes 200b. The display of these supplemental genes is optional. To avoid confusion regarding gene positions, it may be preferable for this supplementary expression information to remain hidden until the user specifically calls for its display, such as by clicking with a mouse on the textual site information 320. This view, like the others described above, may be used with a software package that shows several different views simultaneously and with linked selectability, such as that described with regard to FIGS. 7A-7B above, for example. In this case, another view with a pathway viewer can be linked to this view so that the positions and expression levels of all transcription-related genes may be highlighted simultaneously in multiple views.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

That which is claimed is:

1. A computer-implemented method for overlaying gene- or protein-related data on chromosome maps to provide at least one data-enhanced chromosome map as an output, said method comprising:
   receiving said chromosome maps as a first input to a computer;
   receiving a list comprising a plurality of gene- or protein-related data items as a second input to said computer, each data item including data other than data specifying a genetic location on said chromosome maps;
   providing an identifier specifying a genetic location for each of said data items on said chromosome maps;
   matching said identifiers with predefined identifiers on at least one of said chromosome maps;
   reordering said data items to an order matching the order of said predefined identifiers on said at least one of said chromosome maps; and
   displaying said data items on said at least one chromosome map at locations determined by said reordered data items to provide said data-enhanced output, wherein said displaying includes simultaneously displaying a high-level view of said at least one chromosome map, a mid-level view of a portion of said high-level view, and a detailed view including detailed information of said selected portion, wherein said views are interlinked so that changing one of said views automatically changes the other of said views, wherein said receiving, matching, reordering and displaying are carried out automatically by said computer.

2. The method of claim 1, further comprising interactive selection by a user of at least one data type to be displayed during said displaying.

3. The method of claim 1, further comprising spatially grouping said gene- or protein-related data to correspond to spatial groupings of said associated genes on said at least one chromosome map.

4. The method of claim 1, further comprising compressing said gene- or protein-related data when required to display said gene- or protein-related data in an area in which all of the gene- or protein-related data cannot be discretely displayed.

5. The method of claim 1, further comprising zooming at least one of said gene- or protein-related data and said at least one chromosome map to display an enlarged view of additional detail relevant to a zoomed area.

6. The method of claim 1, further comprising querying and cutting information on the display that a user is not interested in viewing.

7. The method of claim 1, wherein said at least one chromosome map comprises a plurality of chromosome maps, said method further comprising maintaining focus and context of at least a portion of the display of said chromosome maps and gene- or protein-related data by displaying at least one chromosome map with overlaid gene- or protein-related data at a first magnification and at least one other chromosome map with overlaid gene- or protein-related data at a second magnification, so that said one map and said one other map are viewed simultaneously, said first magnification being different from said second magnification.

8. The method of claim 1, wherein said at least one chromosome map comprises a plurality of chromosome maps, said method further comprising maintaining focus and context of at least a portion of the display of said chromosome maps and gene- or protein-related data by simultaneously displaying said high level view of all of said chromosome maps and gene- or protein-related data, said mid-level view displaying a magnified view of said selected portion of said high level view, and said detailed view displaying said detailed information characterizing a selected portion of said mid-level view.

9. The method of claim 8, wherein changing one of said high-level view, mid-level view and detailed view automatically changes the other two views in the same way, substantially simultaneously.

10. The method of claim 1, further comprising displaying tooltips to display additional details relative to a selected portion of the display.

11. The method of claim 1, further comprising displaying popup dialogs to display additional details relative to a selected portion of the display.

12. The method of claim 1, further comprising accessing an external source of information relative to the data displayed, matching at least one of said identifiers with specific information in said external source; and displaying said specific information relative to said gene- or protein-related data associated with said at least one identifier, wherein said specific information comprises data other than markers, identifiers, or a chromosome map.

13. The method of claim 1, wherein said identifiers of said gene- or protein-related data are selected from published gene identifiers and symbols.

14. The method of claim 13, wherein said published gene identifiers and symbols are selected from at least one of GenBank accession numbers, RefSeq accession numbers, UniGene Cluster ID's, UniGene ID's, LocusLink ID, SwissProt ID's, and Protein Information Resource (PIR) ID's.

15. The method of claim 1, wherein said matching comprises providing a relational database which stores a set of cross-referenced tables for matching said identifiers with said predefined identifiers, and as the identifiers are read, they are matched with said predefined identifiers in the cross-referenced tables through standard database queries.

16. The method of claim 1, wherein said gene- or protein-related data comprises an expression matrix having rows and columns, wherein each said row of said matrix contains data values for a particular gene or protein across a set of measured samples, and results of each said measured sample are provided by data in respective columns of said matrix.

17. The method of claim 16, wherein said gene- or protein-related data comprises a plurality of expression matrices.

18. The method of claim 1, wherein said gene- or protein-related data comprises a matrix of at least one microarray of gene expression data, wherein each row of the matrix is associated with a particular gene, with data in the respective row being associated with said particular gene, and wherein said matching comprises reordering and spatial grouping of the rows based on matching the identifiers to the predefined identifiers.

19. The method of claim 18, wherein a visualization of the matrix resultant from said displaying comprises a heat map.

20. The method of claim 18, further comprising calculating row vectors of the values in the rows of the matrix; using an auxiliary process to obtain cluster data for said row vectors; and displaying said cluster data along side said display of said gene- or protein-related data.

21. The method of claim 20, wherein said matrix comprises a heat map, and wherein said cluster data and said gene- or protein-related data are displayed with color coding.

22. The method of claim 20, wherein said cluster data is displayed in a single column adjacent each matrix of gene- or protein-related data.

23. The method of claim 20, wherein said cluster data is displayed in a multi-column matrix adjacent each matrix of gene- or protein-related data.

24. The method of claim 1, further comprising statistically assessing co-location values and displaying assessed co-location statistical significance along side said gene- or protein-related data.

25. The method of claim 1, further comprising the steps of:
selecting additional information characterizing said gene- or protein-related data; and
displaying said additional information along side of said display of the gene- or protein-related data and positioned relative to the respective locations on the chromosome map of the respective genes characterized by said gene- or protein-related data.

26. The method of claim 25, wherein said additional information comprises annotations.

27. The method of claim 26, wherein said annotations comprise gene ontology annotations.

28. The method of claim 26, wherein said gene- or protein-related data is displayed in matrix format and said additional information is displayed in at least one additional matrix.

29. The method of claim 25, wherein said additional information is selected from the group consisting of CGH data, protein levels, relevance scores and relevance densities.

30. The method of claim 25, wherein said gene- or protein-related data is displayed in scatter plot format.

31. The method of claim 25, wherein said additional information includes at least one of annotations, cellular localization of the genetic material, cluster data, and statistical data.

32. The method of claim 1, wherein said gene- or protein-related data is imported from a plurality of experiments.

33. The method of claim 32, wherein said gene- or protein-related data is displayed with regard to each of the plurality of experiments on a single display.

34. The method of claim 1, wherein said gene- or protein-related data comprises a matrix of at least one microarray of gene expression data, wherein each row of the matrix is associated with a particular gene, and wherein each column of the matrix is associated with a microarray experiment, wherein a portion of the total number of columns are associated with experiments taken from normal, healthy tissue, and another portion of the total number of columns are associated with experiments taken from tissue exhibiting an abnormality, said method further comprising dividing the matrix into two smaller matrices with a first matrix containing the columns associated with normal experiments and a second matrix containing the columns associated with abnormal experiments, and wherein said matching and displaying are performed with regard to both first and second matrices.

35. The method of claim 34, wherein the first and second matrices are displayed in color coding as heat maps.

36. The method of claim 34, further comprising calculating a relevance score for at least one row of the matrices by comparing expression values in the first matrix with expression values in the second matrix, and displaying at least one calculated relevance score along side the row to which each pertains.

37. The method of claim 36 wherein said calculating is interactively initiated via a user interface.

38. The method of claim 36, wherein the relevance score comprises a "p value" and the relevance score is displayed as a value calculated by (−log p value).

39. The method of claim 36, wherein a plurality of relevance scores is calculated and displayed as a line map.

40. The method of claim 36, wherein a plurality of relevance scores is calculated and displayed in color-coding as a heat map.

41. The method of claim 36, wherein relevance scores are calculated and displayed in a binary code.

42. The method of claim 36, wherein a plurality of relevance scores is calculated, said method further comprising defining a relevance density score based upon distances between genetic locations and relevance scores, and identifying chromosomal locations containing relevance density scores greater than or equal to the defined relevance density score.

43. The method of claim 36, wherein a plurality of relevance scores is calculated, said method further comprising filtering the relevance scores by setting at least one relevance score limit value and displaying only those relevance scores which are greater than or equal to at least one relevance score limit value.

44. The method of claim 34, further comprising matching chromosomal copy number abnormality data with the gene-related data identifiers, and displaying the chromosomal copy number abnormality data along side the gene-related data to which each is matched.

45. The method of claim 44, wherein the chromosomal copy number abnormality data is displayed in third and fourth matrices, wherein each value in the third matrix is matched with the expression value in the first matrix having the same row and column location, and wherein each value in the fourth matrix is matched with the expression value in the second matrix having the same row and column location.

46. The method of claim 45, further comprising calculating a relevance score for at least one row of the chromosomal copy number abnormality data by comparing chromosomal copy number abnormality values in the third matrix with chromosomal copy number abnormality values in the fourth matrix, and displaying at least one calculated relevance score along side the row to which each pertains.

47. The method of claim 46, wherein the relevance score comprises a "p value" and the relevance score is displayed as a value calculated by (−log p value).

48. The method of claim 46, wherein a plurality of relevance scores is calculated and displayed as a line map.

49. The method of claim 46, wherein a plurality of relevance scores is calculated and displayed in color-coding as a heat map.

50. The method of claim 46, wherein a plurality of relevance scores is calculated, said method further comprising defining a relevance density score based upon distances between genetic locations and relevance scores, and identifying chromosomal locations containing relevance density scores greater than or equal to the defined relevance density score.

51. The method of claim 46, wherein a plurality of relevance scores is calculated, said method further comprising filtering the relevance scores by setting at least one relevance score limit value and displaying only those relevance scores which meet or exceed at least one relevance score limit value.

52. The method of claim 44, wherein the chromosomal copy number abnormality data is provided in columns interlaced with the columns of expression data in the first and second matrices.

53. The method of claim 44, wherein the chromosomal copy number abnormality is displayed in color-coding, as one or more heat maps.

54. The method of claim 44, wherein the chromosomal copy number abnormality data is displayed as one or more line maps.

55. The method of claim 1, further comprising the steps of:
selecting additional information related to one or more genes characterized by said gene- or protein-related data; and
displaying said additional information along side of said display of the gene- or protein-related data and positioned relative to the respective locations on the chromosome map of the respective genes characterized by said gene- or protein-related data.

56. The method of claim 55, wherein said additional information comprise at least one of polymorphism measurements, annotations, transcription factor binding sites, RNA expression values, allele information, alternative exon splicing data, mapping of CGH gene amplification/deletions, and protein abundance.

57. A computer-implemented method for overlaying gene- or protein-related data on chromosome maps to provide a data-enhanced map, said method comprising:
receiving said chromosome maps as a first input to a computer;
receiving a list comprising a plurality of gene- or protein-related data items as a second input to said computer, each data item including data other than data specifying a genetic location on said chromosome maps;
providing an identifier specifying a genetic location for each of said data items on said chromosome maps;
matching said identifiers with predefined identifiers on at least one of said chromosome maps;
reordering said data items to an order matching the order of said predefined identifiers on said at least one of said chromosome maps; and
displaying said data items on said at least one chromosome map at locations determined by said reordered data items to provide said data enhanced map, wherein said displaying includes simultaneously displaying a high-level view of said chromosome maps, a mid-level view of a portion of said high-level view, and a detailed view including detailed information of said selected portion, wherein said views are interlinked so that changing one of said views automatically changes the other of said views, wherein said receiving, matching and displaying are carried out automatically by said computer and wherein said gene- or protein-related data comprises a matrix of at least one microarray of gene expression data, wherein each row of said matrix is associated with a particular gene, and wherein each column of said matrix is associated with a microarray experiment, wherein a portion of the total number of columns is associated with experiments taken from normal, healthy tissue, and another portion of the total number of columns is associated with experiments taken from tissue exhibiting an abnormality,
said method further comprising dividing said matrix into two smaller matrices with a first matrix containing the columns associated with normal experiments and a second matrix containing the columns associated with abnormal experiments, and wherein said matching and displaying are performed with regard to both first and second matrices.

58. The method of claim 57, wherein the first and second matrices are displayed in color coding as heat maps.

59. The method of claim 57, further comprising calculating a relevance score for at least one row of the matrices by comparing expression values in the first matrix with expression values in the second matrix, and displaying at least one calculated relevance score along side the row to which each pertains.

60. The method of claim 59, wherein said calculating is interactively initiated via a user interface.

61. The method of claim 59, wherein the relevance score comprises a "p value" and the relevance score is displayed as a value calculated by (−log p value).

62. The method of claim 59, wherein a plurality of relevance scores is calculated and displayed as a line map.

63. The method of claim 59, wherein a plurality of relevance scores is calculated and displayed in color-coding as a heat map.

64. The method of claim 59, wherein relevance scores are calculated and displayed in a binary code.

65. The method of claim 59, wherein a plurality of relevance scores is calculated, said method further comprising defining a relevance density score based upon distances between genetic locations of genes to which said gene-related data are associated, and relevance scores of the gene-related data, and identifying chromosomal locations containing relevance density scores greater than or equal to the defined relevance density score.

66. The method of claim 59, wherein a plurality of relevance scores are calculated, said method further comprising filtering the relevance scores by setting at least one relevance score limit value and displaying only those relevance scores which are greater than or equal to at least one relevance score limit value.

67. The method of claim 57, further comprising matching chromosomal copy number abnormality data with the gene-related data identifiers, and displaying the chromosomal copy number abnormality data along side the gene-related data to which each is matched.

68. The method of claim 67, wherein the chromosomal copy number abnormality data is provided in columns interlaced with the columns of expression data in the first and second matrices.

69. The method of claim 67, wherein the chromosomal copy number abnormality is displayed in color-coding, as one or more heat maps.

70. The method of claim 67, wherein the chromosomal copy number abnormality data is displayed as one or more line maps.

71. A computer facilitated method for overlaying gene- or protein-related data on chromosome maps, said method comprising:
receiving a list comprising a plurality of gene- or protein-related data items as an input to a computer, each data item having identifiers specifying a genetic location for each of said data items on said chromosome maps;
matching the identifiers with predefined identifiers on at least one of the chromosome maps:
displaying the data items on the at least one chromosome map where the genes associated with the respective data items are located, wherein said displaying includes simultaneously displaying a high-level view of said chromosome maps, a mid-level view of a portion of said high-level view, and a detailed view including detailed information of said selected portion, wherein said views are interlinked so that changing one of said views automatically changes the other of said views, wherein said receiving, matching and displaying are carried out automatically by said computer, and wherein said gene- or protein-related data comprises a matrix of at least one microarray of gene expression data, wherein each row of the matrix is associated with a particular gene, and wherein each column of the matrix is associated with a microarray experiment, wherein a portion of the total number of columns are associated with experiments taken from normal, healthy tissue, and another portion of the total number of columns are associated with experiments taken from tissue exhibiting an abnormality,
dividing the matrix into two smaller matrices with a first matrix containing the columns associated with normal experiments and a second matrix containing the columns associated with abnormal experiments, wherein said matching and displaying are performed with regard to both first and second matrices; and
matching chromosomal copy number abnormality data with the gene-related data identifiers, and displaying the chromosomal copy number abnormality data along side the gene-related data to which each is matched, wherein the chromosomal copy number abnormality data is displayed in third and fourth matrices, wherein each value in the third matrix is matched with the expression value in the first matrix having the same row and column location, and wherein each value in the fourth matrix is matched with the expression value in the second matrix having the same row and column location.

72. The method of claim 71, further comprising calculating a relevance score for at least one row of the chromosomal copy number abnormality data by comparing chromosomal copy number abnormality values in the third matrix with chromosomal copy number abnormality values in the fourth matrix, and displaying at least one calculated relevance score along side the row to which each pertains.

73. The method of claim 72, wherein the relevance score comprises a "p value" and the relevance score is displayed as a value calculated by ($-\log$ p value).

74. The method of claim 72, wherein a plurality of relevance scores is calculated and displayed as a line map.

75. The method of claim 72, wherein a plurality of relevance scores is calculated and displayed in color-coding as a heat map.

76. The method of claim 72, wherein a plurality of relevance scores is calculated, said method further comprising defining a relevance density score based upon distances between genetic locations and relevance scores, and identifying chromosomal locations containing relevance density scores greater than or equal to the defined relevance density score.

77. The method of claim 72, wherein a plurality of relevance scores is calculated, said method further comprising filtering the relevance scores by setting at least one relevance score limit value and displaying only those relevance scores which meet or exceed at least one relevance score limit value.

* * * * *